United States Patent
Mazzeo et al.

(10) Patent No.: US 9,909,974 B2
(45) Date of Patent: Mar. 6, 2018

(54) DATA ACQUISITION SYSTEM WITH ROTATING PROBE MEMBERS AND GROUND REFERENCE ELECTRODE

(71) Applicant: BRIGHAM YOUNG UNIVERSITY, Provo, UT (US)

(72) Inventors: Brian A. Mazzeo, Provo, UT (US); W. Spencer Guthrie, Provo, UT (US); Warren Kemmerer, Provo, UT (US); Jared Baxter, North Ogden, UT (US); Chloe Roedel, Provo, UT (US)

(73) Assignee: Brigham Young University, Provo, UT (US)

( * ) Notice: Subject to any disclaimer, the term of this patent is extended or adjusted under 35 U.S.C. 154(b) by 249 days.

(21) Appl. No.: 14/698,788

(22) Filed: Apr. 28, 2015

(65) Prior Publication Data
US 2015/0362422 A1    Dec. 17, 2015

Related U.S. Application Data

(60) Provisional application No. 61/996,065, filed on Apr. 28, 2014, provisional application No. 62/115,123, filed on Feb. 11, 2015.

(51) Int. Cl.
    *G01N 27/20*    (2006.01)
    *G01N 17/00*    (2006.01)
    *G01N 33/38*    (2006.01)

(52) U.S. Cl.
    CPC .......... *G01N 17/006* (2013.01); *G01N 27/20* (2013.01); *G01N 33/383* (2013.01)

(58) Field of Classification Search
    CPC ..... G01N 17/006; G01N 33/383; G01N 27/20
    See application file for complete search history.

(56) References Cited

U.S. PATENT DOCUMENTS

| 4,401,548 A | 8/1983 | Brezinski |
| 4,568,873 A * | 2/1986 | Oyanagi ............ G01B 7/023 324/627 |
| 4,861,453 A | 8/1989 | Matsuoka et al. |
| 5,069,774 A | 12/1991 | Hladky et al. |

(Continued)

FOREIGN PATENT DOCUMENTS

| JP | 2002-286623 A | 10/2002 |
| WO | 2012/009635 A2 | 1/2012 |

(Continued)

OTHER PUBLICATIONS

International Search Report and Written Opinion received for PCT Patent Application No. PCT/US2015/028091, dated Feb. 17, 2016, 9 pages.

(Continued)

*Primary Examiner* — J. Christopher Ball
(74) *Attorney, Agent, or Firm* — Brake Hughes Bellermann LLP

(57) ABSTRACT

In one general aspect, an apparatus can include a probe including a plurality of exterior rotating members defining a guard ring, and an interior rotating member having a circular shape and disposed within at least a portion of a perimeter defined by the plurality of exterior rotating members. The apparatus can also include a waveform generator electrically coupled to the guard ring and the interior rotating member.

23 Claims, 11 Drawing Sheets

(56) References Cited

U.S. PATENT DOCUMENTS

| | | | |
|---|---|---|---|
| 5,259,944 | A | 11/1993 | Feliu et al. |
| 5,370,776 | A | 12/1994 | Chen |
| 5,425,867 | A | 6/1995 | Dawson et al. |
| 5,666,061 | A | 9/1997 | Assenheim |
| 5,674,375 | A | 10/1997 | Thompson |
| 5,792,337 | A | 8/1998 | Padovani et al. |
| 5,895,843 | A | 4/1999 | Taylor et al. |
| 6,151,969 | A | 11/2000 | Miller et al. |
| 6,805,788 | B1 | 10/2004 | Gonzalez-Martin et al. |
| 7,088,115 | B1 | 8/2006 | Glenn et al. |
| 7,466,149 | B1 | 12/2008 | Yang |
| 2002/0190729 | A1 | 12/2002 | Wilson |
| 2005/0211570 | A1 | 9/2005 | Jovancicevic et al. |
| 2007/0229095 | A1 | 10/2007 | Ramgopal et al. |
| 2010/0045311 | A1 | 2/2010 | Chung |
| 2012/0012470 | A1 | 1/2012 | Bartholomew et al. |
| 2014/0260527 | A1 | 9/2014 | Mazzeo et al. |

FOREIGN PATENT DOCUMENTS

| | | | |
|---|---|---|---|
| WO | WO 2013156142 A1 * | 10/2013 | .......... G01N 33/383 |
| WO | 2014165163 A1 | 10/2014 | |
| WO | 2016/014134 A2 | 1/2016 | |

OTHER PUBLICATIONS

"Rapid Concrete Bridge Deck Condition Assessment: Vertical Impedance and Acoustic Impact-Echo Testing", Mar. 30, 2015, 2 pages.

Argyle, Hillary McKenna, "Sensitivity of Electrochemical Impedance Spectroscopy Measurements to Concrete Bridge Deck Properties", Mar. 2014, 151 pages.

Guthrie et al., "Demonstration of Vertical Impedance Testing for Condition Assessment of a Concrete Bridge Deck With an Asphalt Overlay System", Aug. 2014, 38 pages.

Guthrie et al., "Demonstration of Vertical Impedance and Acoustic Impact-Echo Testing for Condition Assessment of a Concrete Bridge Deck With a Concrete Overlay and a Polymer Surface Treatment", Sep. 2014, 71 pages.

Guthrie et al., "Vertical Impedance Testing for Condition Assessment of a Concrete Bridge Deck with an Asphalt Overlay System", Jan. 6, 2015, 12 pages.

"Florida Method of Test for Concrete Resistivity as an Electrical Indicator of its Permeability", Designation: FM5-578, Jan. 27, 2004, pp. 1-4.

"Resistivity Meter Calibration Box", CNS Farnell Limited, Resistivity Measurement in Concrete, 2005 (Copyright), 1 page.

"RM MK II Concrete Resistivity Metter Model U95", CNS Farnell Limited, RM Concrete Resistivity Meter Operating Manual, Operating Instructions, 2008 (Copyright), pp. 1-16.

"RM-8000 Resistivity Meter", NDT James Instruments Inc., Instruction Manual, 5 pages.

"VersaSTAT 3 Hardware Manual", 2003, 30 pages.

Ewins, A. J., "Resistivity Measurements in Concrete", British Journal of NDT, vol. 32, No. 3, Mar. 1990, pp. 120-126.

Kessler, R. J., et al., "Resistivity Measurements of Water Saturated Concrete as an Indicator of Permeability", Corrosion, Corrosion Research Paper # 000553, 2005, pp. 1-10.

Millard, S. G., "Reinforced Concrete Resistivity Measurement Techniques", Structural and Building Board, Paper 9674, Proc. Instn. Civ. Engrs., Part 2, vol. 91, 1991, pp. 71-88.

Millard, S. G., et al., "Measurements of the Electrical Resistivity of Reinforced Concrete Structures for the Assessment of Corrosion Risk", British Journal NDT, vol. 31, No. 11, Nov. 1989, pp. 617-621.

Millard, S. G., et al., "Practical Measurement of Concrete Resistivity", British Journal of NDT, Resistivity Paper, vol. 33, No. 2, Feb. 1991, pp. 59-63.

Pradhan et al., "Performance evaluation of rebar in chloride contaminated concrete by corrosion rate", Construction and Building Materials, vol. 23, pp. 2346-2356, 2009.

Bartholomew, et al., "Vertical impedance measurements on concrete bridge decks for assessing susceptibility of reinforcing steel to corrosion", AIP Review of Scientific Instruments, vol. 83, 8 pages, Aug. 9, 2012.

"Bridge & Parking Decks"; NDE Condition Assessment; Olsen Engineering; 5 pages [available on Mar. 30, 2016 per https://web.archive.org/web/20160330174354/http://olsonengineering.com/services/concrete-bridge-deck-scanning.html].

Olson: "Innovations in Bridge Superstructure Condition Assessment with Sonic and Radar Methods," published in ASNT Structure Materials Technology Conference, La Guardia, New York, 2010, 12 pages.

* cited by examiner

DATA ACQUISITION SYSTEM WITH ROTATING PROBE MEMBERS AND GROUND REFERENCE ELECTRODE

RELATED APPLICATIONS

This application claims priority to and the benefit of U.S. Provisional Patent Application Ser. No. 61/996,065, filed on Apr. 28, 2014, entitled, "Rolling Electrochemical Impedance Spectroscopy Probe for Interrogating Cover Protection of Rebar" and claims priority to and the benefit of U.S. Provisional Patent Application Ser. No. 62/115,123, filed on Feb. 11, 2015, "Data Acquisition System and Large Relative Area Electrode," both of which are incorporated herein by reference in their entireties.

FEDERALLY SPONSORED RESEARCH

This invention was made with government support under contract W91156-12-P-0185 awarded by the U.S. Army Dugway Proving Ground. The government has certain rights in the invention.

TECHNICAL FIELD

This description relates to methods and apparatus for analysis of concrete.

BACKGROUND

Corrosion of reinforcing steel in reinforced concrete structures (e.g., concrete parking garages, reinforced slabs on grade, concrete retaining walls, concrete buildings, water tank lids) is a pressing problem affecting hundreds of thousands of concrete structures such as concrete bridges. For example, the United States Federal Highway Administration has estimated that a relatively large portion (e.g., 15%) of the hundreds of thousands of bridges in the United States have been structurally compromised due to corrosion. The cost to repair or replace these highway bridges is estimated to be billions of dollars. Corrosion can be caused by, for example, chloride ions introduced to the surface of a concrete bridge deck when de-icing salts are applied to melt snow and remove ice from the area. The decision to, for example, repair or replace these concrete bridges depends largely on the corrosion state of the reinforcing bars installed within the concrete bridges and on assessments of the condition of the concrete cover over the reinforcement.

Using known techniques, assessing the condition of the concrete cover over reinforcing bars within concrete structures cannot be performed in a desirable fashion. For example, destructive, invasive methods can be used to physically examine the internal state of the concrete structure and measure the chloride content. However, these techniques may be undesirable in some situations because they require the destruction of portions of the structure. Known acoustic methods and ground penetrating radar methods can provide information about delamination and geometrical changes within the concrete, but these are generally late-stage corrosion indicators. Electrochemical methods, such as half-cell potential measurements and linear polarization, give information about the instantaneous probability and rate of reinforcement corrosion within the structure, but these known electrochemical methods do not provide direct information about the condition of the concrete cover. Concrete resistivity methods can provide information about the quality of the concrete cover but may not provide direct information about the condition of the reinforcing steel; furthermore, resistivity methods can require precise conditions (e.g., precise solutions) and/or procedures to be performed with success and may not have desirable accuracy and/or coverage. In addition, some known instruments may only work in a laboratory setting where the reinforcing bars can be isolated from earth ground. In a field setting on, for example, a bridge deck, the electrical network of the bridge may be coupled to the earth ground, and, consequently, current monitoring using known instruments can yield questionable results. In addition, known systems used for measuring the properties of roads and bridges may be inefficient in collecting and analyzing data. Thus, a need exists for systems, methods, and apparatus to address the shortfalls of present technology and to provide other new and innovative features.

SUMMARY

In one general aspect, an apparatus can include a probe including a plurality of exterior rotating members defining a guard ring, and an interior rotating member having a circular shape and disposed within at least a portion of a perimeter defined by the plurality of exterior rotating members. The apparatus can also include a waveform generator electrically coupled to the guard ring and the interior rotating member.

DETAILED DESCRIPTION

Figure 1:
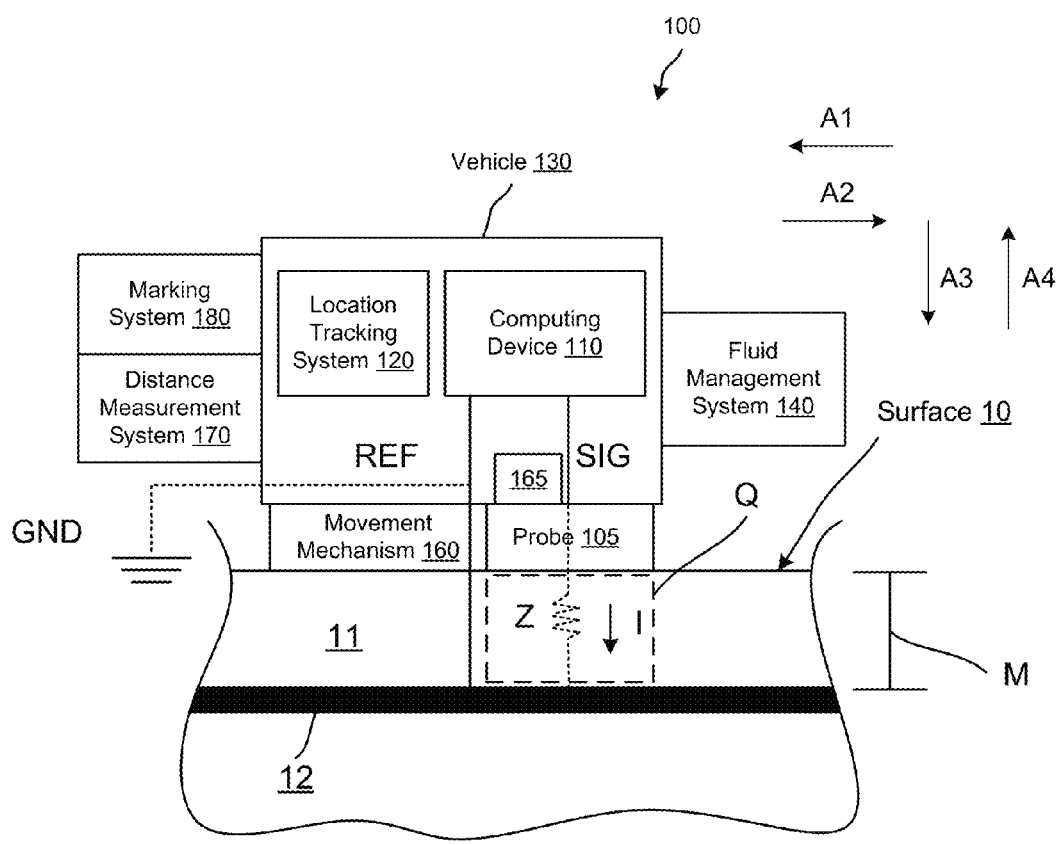
FIG. 1 is a diagram that illustrates a data acquisition system used to acquire data.

FIG. 1 is a diagram that illustrates a data acquisition system 100 (also can be referred to as a system, as a concrete analysis system, or as a mobile data acquisition system) according to at least one implementation. As shown in FIG. 1, the data acquisition system 100 includes a computing device 110 (which can also be referred to as a concrete analyzer) and a probe 105. The computing device 110 can include, for example, a waveform generator (which is discussed in more detail below). The computing device 110 can be used to control operations of, for example, test data acquisition (e.g., impedance measurement acquisition). Although many of the implementations here are described in the context of rebar (or another conductive material) in concrete, other materials can be interrogated (also can be referred to as tested) using the data acquisition system 100. Some examples of structures that can be interrogated using the system 100 include, but are not limited to, concrete parking garages, reinforced slabs on grade, concrete retaining walls, concrete buildings, water tank lids, and/or so forth.

The probe 105 is configured to be coupled to (e.g., in contact with) a surface 10 of concrete 11 (or another material) that includes a reinforcing bar 12 installed within (e.g., embedded within) the concrete 11. The probe 105 is electrically coupled to a signal node SIG of the computing device 110. The reinforcing bar 12 and the computing device 110 are electrically coupled to a common ground represented as ground node GND. Accordingly, the computing device 110 is grounded to the reinforcing bar 12. Although not shown, in some implementations, the reinforcing bar 12 and the computing device 110 can be coupled to a common reference that is separate from the ground node GND. In some implementations, the data acquisition system 100 can reference a potential of the reinforcing bar 12, which can function as a reference potential and/or as a ground. A variety of grounding techniques are described below in more detail in connection with several of the figures.

The data acquisition system 100 is configured to determine (e.g., calculate, detect, measure) an impedance Z of a region Q of the concrete 11 using impedance spectroscopy techniques. In some implementations, the region Q can be referred to as a target analysis region. As shown in FIG. 1, the region Q, which can represent a volume, is approximately disposed between the surface 10 of the concrete 11 and the reinforcing bar 12 in a cover portion of the concrete 11 having a thickness M. The region Q is an approximate representation of a volume of the concrete 11 for which the impedance Z is determined (e.g., calculated). In some implementations, the impedance Z of the concrete 11 within the region Q can be approximated by the data acquisition system 100.

Although not shown in FIG. 1, the reinforcing bar 12 can be disposed within a plane (not shown) that is parallel to, or approximately parallel to, the surface 10 of the concrete 11. In some implementations, the reinforcing bar 12 can be part of a mat or a mesh (e.g., a relatively planar mat or mesh) of reinforcing bars embedded within the concrete 11 so that the concrete is reinforced concrete.

The probe 105 of the system 100 is configured to interrogate the condition of concrete/asphalt/polymer or other material disposed around (e.g., protecting) rebar or another conductive material (e.g., rebar 12) in a relatively rapid fashion. In some implementations, the probe 105 can include one or more rotating members (e.g., rolling mechanisms) (not shown in FIG. 1) so that the probe can be moved in a lateral direction (e.g., lateral direction A1 or lateral direction A2) while still contacting the surface 10 for interrogation. The rotating members can be rotating electrodes.

In some implementations, the probe 105 can include a rotating member (which can function as an electrode or as an active electrode) surrounded at least partially by a guard ring. In some implementations, the active electrode and guard ring can each have a bottom surface aligned along a same plane. The guard ring can also include at least one rotating member. In some implementations, the probe 105 can include a central rotating member (e.g., a central rolling electrode, an active electrode) at least partially surrounded by several rotating members that define a guard ring (e.g., a rolling guard ring). The use of such a configuration with rotating members can allow for relatively fast and continuous (or periodic or randomly spaced) collection of impedance spectroscopy data (also can be referred to as test data or probe data), which can represent the permeability of the cover protection and/or the presence of significant corrosion enhancers such as chlorides. Accordingly, the probe 105 can be a rolling probe that can be used in conjunction with an electrochemical impedance spectroscopy (EIS) testing device. The probe 105, which can include rotating members, can enable not only fast test data collection, but can also enable continuous test data collection on, for example, the surface 10. Any data collected using the probe 105 can be referred to as test data or as probe data.

The system 100 can be configured to collect test data at discrete locations and/or store this test data in a computer-readable form (e.g., in a memory included in the computing device 100) for plotting, analysis, and interpretation. The data acquisition system 100 can be configured to rapidly take location-referenced test data in real-time to aid an operator in the acquisition of test data sets (e.g., complete data sets), interpretation (e.g., immediate interpretation, real-time interpretation) of data acquired (as well as the possibility of discovering problems during data acquisition), and/or the subsequent immediate use of the test data because it is readily available. The use of the system 100 including the probe 105 can reduce the amount of time to acquire electrochemical impedance spectroscopy test data (or information) on the surface 10 (e.g., a bridge deck). In some implementations, the time to acquire test data using the system 100 can be orders of magnitude faster (on the order of a few seconds) than collection of test data using a conventional system (where collection of test data at a typical single location could on the order of minutes). Electrochemical information can be used to determine information about, for example, the protection of the underlying rebar 12 (under the surface 10) from chloride ingress through the layers of protection surrounding it. The system 100 can be configured to modify and/or prepare the surface 10 (e.g., a wet bridge deck) to enable more rapid measurements.

Although not shown in FIG. 1, the system 100 can include one or more power supplies that can be configured to provide power to one or more portions of the system 100. The power supply can include, for example, a battery, a solar energy device, a generator, and/or so forth.

Figure 2A:
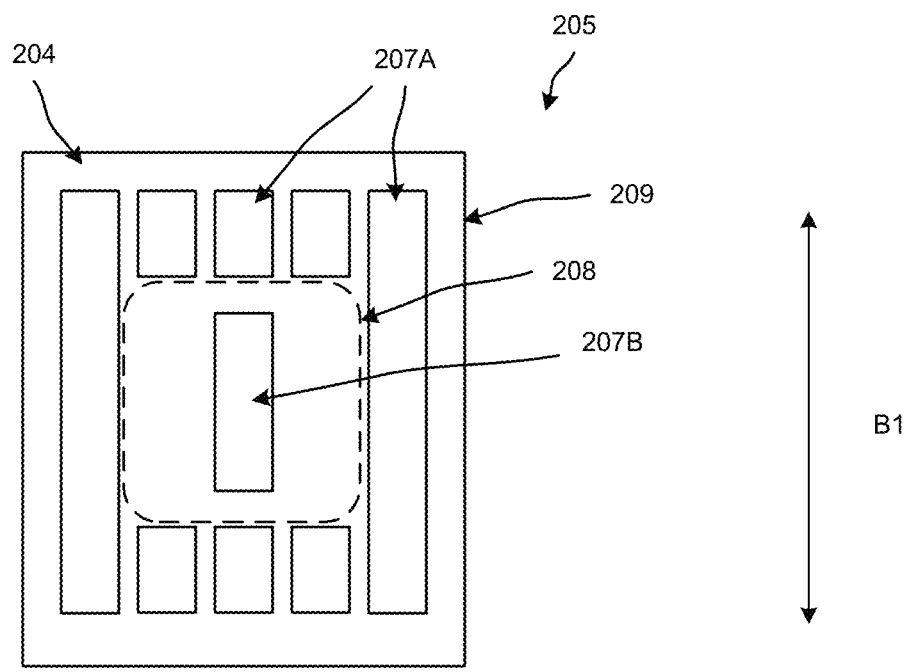
FIGS. 2A and 2B are diagrams that illustrate a bottom view and a side view, respectively, of a probe including rotating members.
Figure 2B:
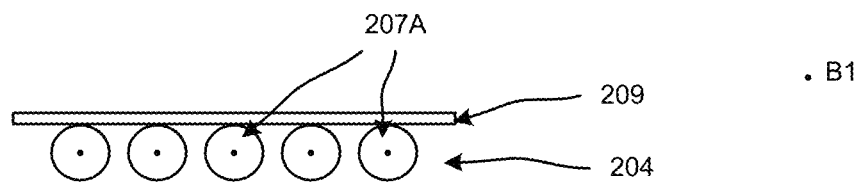

FIGS. 2A and 2B are diagrams that illustrate a bottom view and a side view, respectively, of a probe 205 including rotating members 207A and 207B (which can collective be referred to as rotating members 207). The rotating members 207 can individually or collectively function as electrodes. As shown in FIG. 2A, rotating members 207A (which can be referred to as exterior rotating members or as a guard ring rotating member) define a guard ring 204 around rotating member 207B (which can be referred to as an interior rotating member or an active rotating member). For simplicity, only a few of the rotating members 207A defining the guard ring 204 are labeled. The rotating members 207A define an entirety of, or at least a portion of, a perimeter 208 (illustrated in FIG. 2A as a dashed line). Accordingly, the rotating members 207A entirely or at least partially surround the rotating member 207B.

In some implementations, the perimeter 208 can intersect the rotating members 207A, or can be around an outside of the rotating members 207A. In some implementations, at least some gaps may (or may not) be disposed between pairs of the rotating members 207A; however, a length (or width/distance) of gaps between the rotating members 207A can be less than a length (or width/distance) of a gap (in any direction along a plane through the rotating members 207) between the rotating member 207B and the perimeter 208. In some implementations, a gap between the exterior rotating members 207A and the interior rotating member 207B can be approximately uniform (e.g., constant) or non-uniform. The exterior rotating members 207A can be directly electrically coupled (e.g., coupled via a wire). The exterior rotating members 207A can be electrically isolated from or indirectly electrically coupled to (e.g., electrically separated by a driver or other electrical active or passive components) the interior rotating member 207B.

In this implementation, only one rotating member 207B is illustrated as being disposed inside (or within) the perimeter 208 of the guard ring 204 (which includes multiple rotating members 207A). Although not shown, in some implementations, multiple rotating members (similar to rotating member 207B) can be disposed inside (or within) the perimeter 208 of the guard ring 204. If including multiple interior rotating members, the interior rotating members can be directly electrically coupled.

In some implementations, the rotating member 207B can have at least a portion centrally located within the perimeter. In some implementations, the perimeter defined by the rotating members 207A can define a profile or shape having a square shape, a rectangular shape, a triangular shape and/or or so forth. In some implementations, the rotating members 207 can each have the same diameter, or one or more of the rotating members 207 can have a different diameter.

In some implementations, different rotating member diameters may be appropriate for different applications. In some implementations, relatively large rotating members can enable a greater contact area on the concrete and can also move (e.g., roll) in a desirable fashion over bumps, sags, etc. in a surface (e.g., concrete surface). The diameter of the rotating member can therefore be related to the condition of the surface being tested and also to the need for electrical contact with the surface.

In this implementation, the rotating members 207 (e.g., the rotating members 207A that are included in the guard ring 204) can have at least two different lengths. For example, in some implementations, the rotating members 207A included in the guard ring 204 can have the same length or several different lengths (e.g., more than two lengths). In some implementations, the rotating member 207B can have a length different than, or the same as, a length of one or more of the rotating members 207A included in the guard ring 204.

The rotating members 207A and 207B can be rotatably coupled to a support 209. The support 209 can include one or more portions associated with the different rotating members. For example, one portion of the support 209 can be coupled to the rotating members 207A and another portion of the support 209 can be coupled to the rotating member(s) 207B. If including multiple portions, the support 209 portions can be fixedly or removably coupled together.

Although not shown in FIG. 2A or FIG. 2B, one or more of the rotating members can be coupled via one or more axles, brackets, hinges, and/or so forth so that the one or more rotating members 207 can rotate about an axis (illustrate as dots in FIG. 2B). In this implementation, the rotating members 207 are configured to rotate about an axis parallel to line B1. Accordingly, the probe 205 can be configured to be moved along a direction orthogonal to (e.g., substantially orthogonal to line B1). The configuration shown in at least FIGS. 2A and 2B allows the guard ring 204 (and rotating members 207A thereof) surrounding the rotating member 207B in the center to move with the probe 205 and maintain constant (e.g., substantially constant) contact with the surface (e.g., surface 10 in FIG. 1) to be interrogated.

In some implementations, one or more of the rotating members 207 can have a shape or profile that is circular (e.g., cylindrical, spherical). In some implementations, one or more of the rotating members 207 can have a shape or profile (e.g., a cross-sectional shape or profile) that is oval, non-cylindrical, or non-circular.

As shown in FIG. 2B, the rotating members 207 each have an axis (around which each of the rotating members 207 rotates) that is aligned along the plane of the support 209. The rotating members 207 are aligned along a plane that is parallel to or substantially parallel to a plane along which the support 209 is aligned.

One or more of the rotating members 207 an have a fluid retention portion (also can be referred to as a liquid retention portion or as a water-retaining material). In some implementations, the fluid retention portion can be made of a porous material (e.g., relatively porous material) configured to retain a fluid. For example, the fluid retention portion can include a sponge, a foam, and/or so forth. The entirety of the rotating member 207 can be made of a material that can function as a fluid retention portion. In some implementations, only a portion of the rotating member 207 can be made of a material that can function as a fluid retention portion, such as an outer portion of a cylinder of the rotating member 207. In some implementations only a portion of the rotating members 207 can include a fluid retention portion. In other words, one or more of the rotating members 207 may not include or can exclude a fluid retention portion.

In some implementations, a first rotating member 207 can have a fluid retention portion made of a different material than a fluid retention portion of a second rotating member 207. In some implementations, the fluid retention portion can have a sufficiently long nap, thickness, or other means of ensuring that the fluid retention portion 207 of the rotating member maintains constant and uniform electrical contact with a surface (e.g., a tested slab, deck, wall, or other element) during testing. In some implementations, because different surfaces may require different rotating members (for example, rotating members with longer naps may be required for more uneven surfaces), and because the fluid retention portions of the rotating members 207 may also wear out over time, the rotating members 207 can be replaced by a user.

The probe 205 can include a rolling active electrode (e.g., rotating member 207B) and a rolling guard ring (e.g., rotating members 207A) that can be quickly moved over a surface without having to pick up the probe 205 between sequential measurements. Test data can be correlated with distance traversed over the surface to generate line scans of the test data (which is described in more detail below). From these line scans, plots (e.g., contour plots) of test data (e.g., impedance data) over large areas can be produced.

Referring back to FIG. 1, a fluid (e.g., a liquid, water, an ionic solution, a detergent in water) can be applied to at least a portion of the probe 105 and/or the surface 10 (e.g., the probe 105 shown in FIG. 1) before, after, or concurrent with the probe 105 being in contact with (e.g., placed over) the surface 10. In some implementations, the probe 105 and/or the surface 10 can be saturated with the fluid before the probe 105 is in contact with the surface 10. The fluid can be configured to facilitate transfer of electrical signals (e.g., current and/or voltage signals) between the probe 105 and the surface 10. In other words, the fluid can define a conductive interface between the probe 105 and the surface 10 (which can include an ionic compound). The fluid can function as a transitional medium between the probe 105 and the surface 10.

In some implementations, the probe 105 can be configured, for example, with steel wool or other compressible material that can be coupled to a concrete surface in a desirable fashion so that application of a fluid may not be required. In other words, the probe 105 can be configured so that the probe 105 can be coupled to a concrete surface under dry conditions.

Referring back to FIG. 1, the system 100 can be, or can be included in, a vehicle 130 that can be configured to move along a lateral direction (e.g., direction A1 and/or direction A2) on the surface 10. Accordingly, the system 100 can be, or can be included in, for example, a cart, a motorized vehicle, and/or so forth. Accordingly, the vehicle 130 can include one or more handles, levers, motors, and/or so forth that can be used to move the system 100. In some implementations, a feature as simple as a handle can function as a vehicle that can be used to move the probe 105. More details regarding vehicles are described below.

The system 100 (or vehicle 130) can include a movement mechanism 160 (also can be referred to as a support system) that can be used to facilitate movement of the system 100 along the lateral direction (e.g., direction A1 and/or direction A2) on or along the surface 10. Although not shown in FIG. 1, the movement mechanism 160 can include one or more wheels, tracks, motors, rails for sliding, etc. Test data can be acquired by moving (e.g., pushing, pulling, propelling, and/or so forth) the data acquisition system 100 over the surface 10 (e.g., a bridge (concrete or asphalt)) in a pattern (e.g., straight line pattern, diagonal line pattern, curved pattern).

In some implementations, the system 100 can include a lift mechanism 165. The lift mechanism 165 can be configured to move the probe 105 from a stowed configuration (also can be referred to as a refracted configuration or position) to a deployed configuration (which can also be referred to as a testing configuration or position). The lift mechanism can be configured to move the probe 105, for example, to a desired height (for deployment or for movement without the probe 105 on the surface 10).

For example, the lift mechanism 165 can be configured to move the probe 105 in a downward direction (along direction A3) to a deployed configuration where the probe 105 can have at least a portion that comes in contact with the surface 10. The lift mechanism 165 can also be configured to move the probe 105 in an upward direction (along direction A4) to a stowed configuration where the probe 105 is not in contact with or substantially not in contact with the surface 10. When the probe 105 is in the deployed configuration, the system 100 can be configured to collect test data related to the surface 10 (e.g., can be configured to interrogate the surface 10). When the probe 105 is in the stowed configuration, the system 100 can be configured to be moved without the probe 105 coming in contact with the surface 10 so that the probe 105 may not be damaged or worn.

In some implementations, when the probe 105 is in the deployed configuration, at least a portion of the probe 105 and at least a portion of the movement mechanism 160 can be in contact with the surface 10. In some implementations, when the probe 105 is in the deployed configuration, at least a portion of the probe 105 can be in contact with the surface 10, and one or more portions of the movement mechanism 160 may be moved away from the surface 10 so that the one or more portions of movement mechanism 160 may not be in contact with the surface 10.

In some implementations, the lift mechanism 165 can include one or more spacers, bolts, spring mechanisms, motors, straps, chains, gears, levers, pins, locking mechanisms, and/or so forth to maintain or move the probe 105 between the deployed and stowed configurations. For example, in some implementations, the probe 105 can be lowered or raised by insertion of one or more spacers over one or more bolts holding the probe 105 to the vehicle 130 (e.g., cart). In some implementations, the lift mechanism 165 can include one or more components (e.g., springs, cam mechanisms, gear mechanisms, pins, locking mechanisms, straps, etc.) that can allow the probe 105 to move in a variety of directions (e.g., along any of directions A1 through A4) in response to obstacles (e.g., an evenness, rocks, cavities) in the surface 10. In other words, when in the deployed configuration, the probe 105 can be configured to float (without being rigidly maintained at a specific vertical position) to account for potential unevenness in a surface (e.g., surface 10) being tested or interrogated.

In some implementations, to ensure adequate durability for field use, the rotating members 207 on the probe 205 can be configured to have bearings or bushings. The use of bearings or bushings can decrease the possibility that the rotating members 207 will stop rolling (which would impede the normal movement of the probe 205), avoid dragging of the rotating members 207 across a surface (e.g., a surface of a slab, a deck, a wall, or other element), increase the life of the rotating member fluid retention portions, and/or so forth. Other aspects of the probe 205 can be configured to ensure adequate durability, including ruggedized cabling and electrical connections, impact-resistant components, weather-resistant housings for circuitry, and/or so forth.

In some implementations, one or more of the rotating members 207 can be configured to rotate about an axis non-parallel to direction B1 or non-parallel to an axis about which another of the rotating members 207 rotates. In some implementations, each of the rotating members 207A (exterior rotating members) is configured to rotate about an axis parallel to an axis about which the rotating member 207B (interior rotating members) is configured to rotate.

Figure 3:
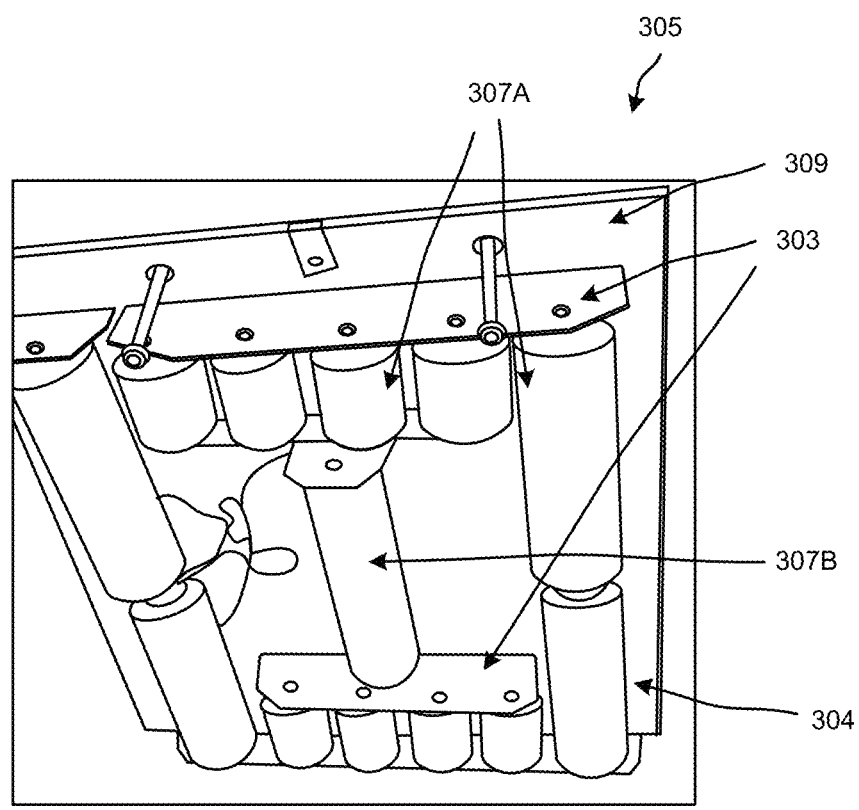
FIG. 3 is a perspective view diagram that illustrates an example of a probe including rotating members.

FIG. 3 is a perspective view diagram that illustrates an example of a probe 305 including rotating members 307. As shown in FIG. 3, the probe 305 includes a central rotating member 307B surrounded by a guard ring 304 including several (e.g., different) rotating members 307A forming a perimeter around the central rotating member 307B. As shown in FIG. 3, brackets 303 are used to couple the rotating members 307 to a support 309 so that the rotating members 307 can each rotate about an axis.

Referring back to at least FIGS. 2A and 2B, one or more of the rotating members 207A and 207B can be electrically coupled to one or more electrical components that can be included in, or associated with a computing device (e.g., computing device 110 shown in FIG. 1, a wave generator included in a computing device, etc.). Although not shown, the electrical connections can be made via a wire, a wire brush, a tab, a protrusion, and/or so forth. In some implementations, for example, to facilitate electrical contact between at least one (e.g., one or more of (e.g., each of)) the rotating members 207 (e.g., rollers) and the circuitry associated with the probe 205, a conductive member (e.g., protrusion, metallic blade, flat member, coupled member) can extend from a plastic sheet or other insulating material (not shown) on the support 209 (which can be made of a conductive or insulating material) to which the at least one rotating member 207 is mounted down to the at least one rotating member 207. The conductive member can be positioned to maintain electrical contact with a fluid retention portion of the at least one rotating member 207 at all times (e.g., as the rotating member rotates). One or more electrical connections can be coupled between the conductive member (e.g., top of the conductive member) and circuity associated with the probe 205.

Figure 4:
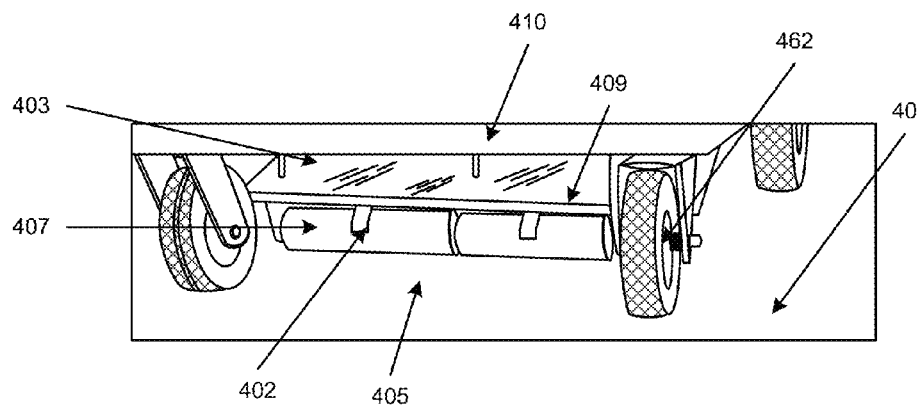
FIG. 4 is a diagram that illustrates a conductive member coupled to a support and in contact with a rotating member.

FIG. 4 is a diagram that illustrates conductive member 402 coupled to a support 409 and in contact with a rotating member 407. The conductive member 402 extends from the support 409 and is in contact with a sidewall of the rotating member 407, and specifically with a fluid retention portion (which is not specifically labeled) of the rotating member 407. The rotating member 407 is rotatably coupled to the support 409. In some implementations, the conductive member 402 can be in contact with the rotating member 407 so that the rotating member 407 can rotate in a first direction (e.g., a clockwise direction) as well as in a second direction (e.g., a counterclockwise direction). In some implementations, more than one conductive member can be coupled to one or more of the rotating members.

In this diagram, a probe 405 is in a deployed configuration so that the rotating member 407 is in contact with a surface 40. When in the deployed configuration, a gap 403 is disposed between a bottom surface of the vehicle 410 and a top of the support 409.

Also, as shown in FIG. 4, a wheel 462 is included as part of a movement mechanism. The wheel 462 of the movement mechanism is independent of (e.g., can rotate independent of) the probe 405 and the rotating member 407. In some implementations, the movement mechanism can be mechanically coupled to the rotating member 407 so that the movement mechanism can move in conjunction with the rotating member 407.

Referring back to FIG. 1, the computing device 110 or a portion thereof (e.g., a waveform generator, a circuit included in the computing device 110) is configured to induce (e.g., inject, cause flow of) a current I (e.g., an instantaneous current, a maximum current, an average current, a root mean square (RMS) current) in the region Q (from the signal node SIG). Based on the current I and based on the voltage drop between the signal node SIG and the reference node REF, the impedance Z of the region Q of the concrete 11 can be calculated (e.g., calculated by the computing device 110). In some implementations, the concrete 11 can be part of a concrete structure such as a concrete parking garage, a reinforced slab on grade, a concrete retaining wall, a concrete building, and/or so forth.

Although many of the implementations described herein are related to the computing device 110 producing a waveform (e.g., a voltage waveform) configured to cause flow of a current in the region Q of the concrete 11, in some implementations, the computing device 110 can be configured to instead produce (e.g., inject) a known current (e.g., a current waveform) into the region Q of the concrete 11. In such implementations, the voltage of the concrete 11 in the region Q can be determined (e.g., measured, derived, calculated) and used to determine an impedance (instead of measuring a current in response to a known voltage waveform to determine an impedance). Accordingly, the techniques described herein can be modified for (e.g., adapted to) various current and/or voltage profiles produced by the computing device 110.

In some implementations, the computing device 110 can be configured to produce a specified current and voltage profile to induce the current I in the region Q. In some implementations, the computing device 110 can be configured to produce, for example, a signal having a specified waveform (also can be referred to as an input waveform) to induce the current I in the region Q. For example, in some implementations, the computing device 110 can be configured to produce a sinusoidal voltage waveform (e.g., an alternating current voltage waveform) (across the signal node SIG to the reference node REF) having a fixed voltage amplitude at a specified frequency. As another example, the computing device 110 can be configured to produce a sinusoidal voltage waveform (across the signal node SIG to the reference node REF) having a fixed voltage amplitude over a range of frequencies. In some implementations, the frequencies of the sinusoidal voltage waveform can be changed over the range of frequencies in a stepwise fashion, a continuous fashion, a random fashion, a periodic fashion, and/or so forth. In some implementations, the frequencies of the sinusoidal voltage waveform can be changed over a range of frequencies in a stepwise fashion, a continuous fashion, a random fashion, a periodic fashion, and/or so forth. In some implementations, the waveform can also include multiple sinusoids and/or white noise superimposed to produce multiple frequency excitations simultaneously.

As yet another example related to current and/or voltage profiles, the computing device 110 can be configured to produce a constant (e.g., steady) (or substantially constant) voltage and/or constant (e.g., steady) (or substantially constant) alternating-current (AC) sinusoidal voltage waveform (across the signal node SIG to the reference node REF) having a fixed voltage amplitude at a specified frequency. In some implementations, the computing device 110 can be configured to produce multiple signals having different profiles simultaneously, in a staggered fashion, in a specified pattern, and/or so forth. In some implementations, the computing device 110 can be configured to produce various types of waveforms including a half-wave waveform. In some implementations, arbitrary waveforms (e.g., square-wave waveforms, random waveforms) can be used by the computing device 110 at relatively low frequencies (e.g., at frequencies below 1 kHz or even below 100 mHz). In some implementations, arbitrary waveforms (e.g., square-wave waveforms, random waveforms) can be used by the computing device 110 at relatively high frequencies (e.g., at frequencies above 1 kHz).

In some implementations, the computing device 110 can be configured to produce a specified current and voltage profile to induce the current I in the region Q during one or more measurement cycles. For example, the computing device 110 can be configured to produce a specified current and voltage profile to induce the current I in the region Q during a first measurement cycle when the probe 105 is placed in the location shown in FIG. 1, and can be configured to produce the same current and voltage profile (or a different current and voltage profile) to induce a current in another region (not shown) during a second measurement cycle when the probe 105 is placed at another location (not shown) on the surface 10 of the concrete 11.

The impedance Z of the region Q of the concrete 11 as determined (e.g., calculated, measured) by the computing device 110 can vary based on a variety of characteristics (e.g., concrete characteristics, concrete attributes) of the concrete 11 including, for example, chloride concentration in the region Q, the thickness M of the concrete cover, coatings (e.g., epoxy coatings) that may be present on the reinforcing bar 12, the quality of the concrete 11 in the region Q (as related to porosity, tortuosity, pore interconnectivity, etc.), degree of water saturation, the temperature of (e.g., temperature profile across) the concrete 11 in the region Q, and/or so forth. Accordingly, the impedance Z of the region Q of the concrete 11 can be an indicator of one or more of the characteristics described above. The characteristics described above can be used to indirectly determine (e.g., ascertain, project) the potential corrosion state of the reinforcing bar 12. Moreover, the characteristics described above can be indicators of the ability of the concrete 11 (or surface treatments that may be topically applied to the concrete 11 to increase protection (impedance measurements and apparatus described herein can be used to identify leaks in such surface treatments)) to protect the reinforcing bar 12 from corrosion (e.g., diffusion of ions that can cause corrosion). Thus, one or more of the characteristics described above can be determined (or identified) based on one or more indicators of the impedance Z of the region Q of the concrete 11. More details related to determination of characteristics of a region of concrete based on impedance (e.g., impedance spectroscopy) are described below.

Figure 5:
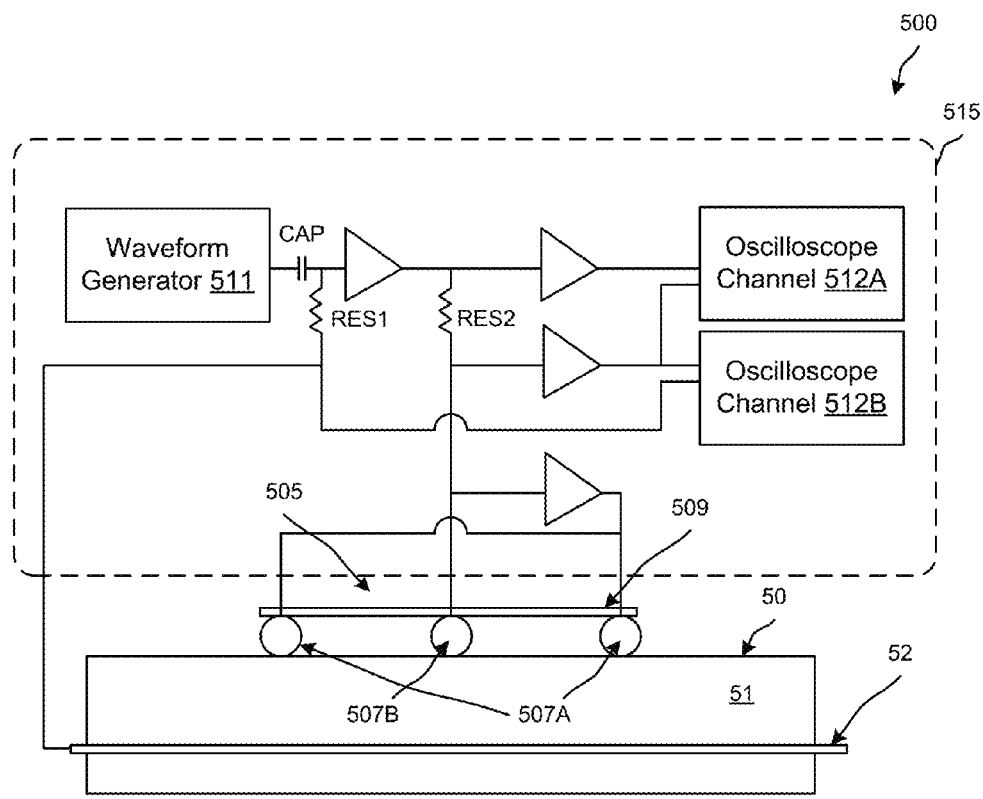
FIG. 5 is a diagram that illustrates a circuit representation of the data acquisition system.

FIG. 5 is a diagram that illustrates a circuit representation of the data acquisition system 500. The data acquisition system 500 includes a circuit 515 and a probe 505. The circuit 515 can be included in, or in communication with, a computing device (e.g., computing device 110 shown in FIG. 1). The circuit 515 includes a waveform generator 511 and oscilloscope channels 512A, 512B. The circuit 515 also includes a capacitor CAP and resistors RES1 and RES2. Circuit drivers are illustrated as triangles. The circuit 515 shown in FIG. 5 is a representation of one possible circuit implementation. Additional components such as capacitors, resistors, inductors, and/or so forth can be included in (or removed from) the circuit 515. The waveform generator 511 may itself be connected directly to the reference node REF.

In some implementations, the capacitor CAP can be, for example, a capacitor having a capacitance value on the order of a few microfarads (e.g., 1 µF). In some implementations, the capacitance value can be greater or less than a few microfarads. In some implementations, the resistor RES1 can have a resistance value that is greater than (e.g., 10 times greater than, 100 times greater than) a resistance value of RES2. For example, the resistor RES1 can have a resistance value of approximately 1 megaOhm (MΩ) and the resistor RES2 can have a resistance value of approximately 10 kiloOhms (kΩ). The value of RES2 may or may not be changed during operation through a system of relays and resistors (not shown) to more accurately measure a range of currents.

The probe includes a support 509 and rotating members 507 (including rotating mechanisms 507A and rotating mechanisms 507). As shown in FIG. 5, at least some portions of the probe 505 are in contact with a surface 50 of a material 51 (e.g., concrete) including a conductor 52 (e.g., rebar) disposed therein.

The circuit 515 is configured to implement a high-side impedance measurement, essentially measuring a current flowing into (e.g., injected into) the material 51 (e.g., concrete cover) over the conductor 52 as a result of a voltage across the material 51. Accordingly, other currents that may be impressed on the conductor 52 may not affect this measurement, which is in contrast to many other electrochemical measurements that use a virtual ground transimpedance configuration. Although not shown in FIG. 5, in some implementations, a voltage sensor, resistor and/or magnetic coupling element can be used to detect a current flowing into the material 51 (e.g., collectively functioning as a current detector).

In some implementations, the waveform generator 511, the two oscilloscope channels 512A, 512B, one or more power supplies (e.g., a +5 V power supply, a −5V power supply) can be integrated into a device (e.g., computing device). In some implementations, the device can be a single USB-powered device. In some implementations, one or more operational amplifier chips can be incorporated into the circuit 515. In some implementations, one or more operational amplifiers with relatively small input bias currents and/or relatively small offset voltages can be implemented in conditions where the impedances that are measured are extremely large. The operational amplifiers can be powered using one or more positive and/or negative power supplies.

The differential oscilloscope channels 512A, 512B enable measurement of the current into and the voltage across a probed region (e.g., a region being interrogated using the probe 505), which then allows calculation of the impedance of the material 51 at a particular location. In another configuration, these oscilloscope channels 512A, 512B may be analog voltage inputs into an alternative computing device.

In some implementations, a waveform generated by the waveform generator 511 can define a waveform at a frequency in, for example, the hundreds of Hertz (Hz) (e.g., 200 Hz). In some implementations, the waveform generator 511 can be configured to define a waveform at a frequency greater than hundreds of Hertz (e.g., in the kHz range or higher) or less than hundreds of Hertz. In some implementations, the magnitude and phase of each of the signals of the oscilloscope channels 512A, 512B can be computed by, for example, multiplying each by cosine and sine followed by a low-pass filtering of the signals. In some implementations, an inner product of one demodulated signal and the complex conjugate of the other demodulated signal can be calculated. Then using that result and the sum of squares of one of the signals, the magnitude and phase difference of the two signals can be calculated. In some implementations, the current-sensing resistor value (e.g., 10 kΩ), for example, can be used to calculate a complex impedance of the material of interest (e.g., material 51).

In some implementations, the circuit 515 can implement an operational electrochemical impedance spectroscopy device. The circuit 515 can include a microcontroller member board, a quad op-amp, a dual op-amp, a multiplexer, and/or a voltage regulator. In some implementations, the circuit 515 can also include a port to couple one or more sensors (e.g., infrared (IR) temperature sensors, air temperature sensors, humidity sensors) to measure the temperature and boundary conditions of a surface (e.g., concrete). In some implementations, the sensor data (e.g., IR temperature sensor data), for example, can be correlated with the impedance measurements, because the impedance of the material (e.g., concrete) can be temperature-dependent. Also, in some implementations, one or more (e.g., 3) resistors can be connected to the multiplexor to ensure that auto-ranging to an impedance measured by a circuit can be performed in a desirable fashion.

Referring back to FIG. 1, the system 100 includes a distance measurement system 170. The distance measurement system 170 can be configured to measure a distance (as distance data) that the system 100 has moved, and the distance data (which can include time data) captured (or calculated) by the distance measurement system 170 can be correlated to test data (e.g., impedance data) collected using the probe 105. In some implementations, the distance measurement system 170 can be coupled to (e.g., behind, along-side) the system 100, and/or integrated into a component thereof. In some implementations, the distance data can be generically included in (or characterized as) location data.

In some implementations, the distance measurement system 170 can include a rotary encoder (not shown). In some implementations, the rotary encoder can be connected to a type of measurement wheel (not shown) that also moves along the surface 10. Signals from the rotary encoder can be converted into counts that can be used to represent distance. Accordingly, the distance traveled by the probe 105 (and correlation to test data collected by the probe 105) when making continuous impedance measurements can be determined. In some implementations, a distance along the surface (e.g., bridge) can be measured using an instrumented axle (e.g., between two wheels of the data acquisition system 100).

Figure 6:
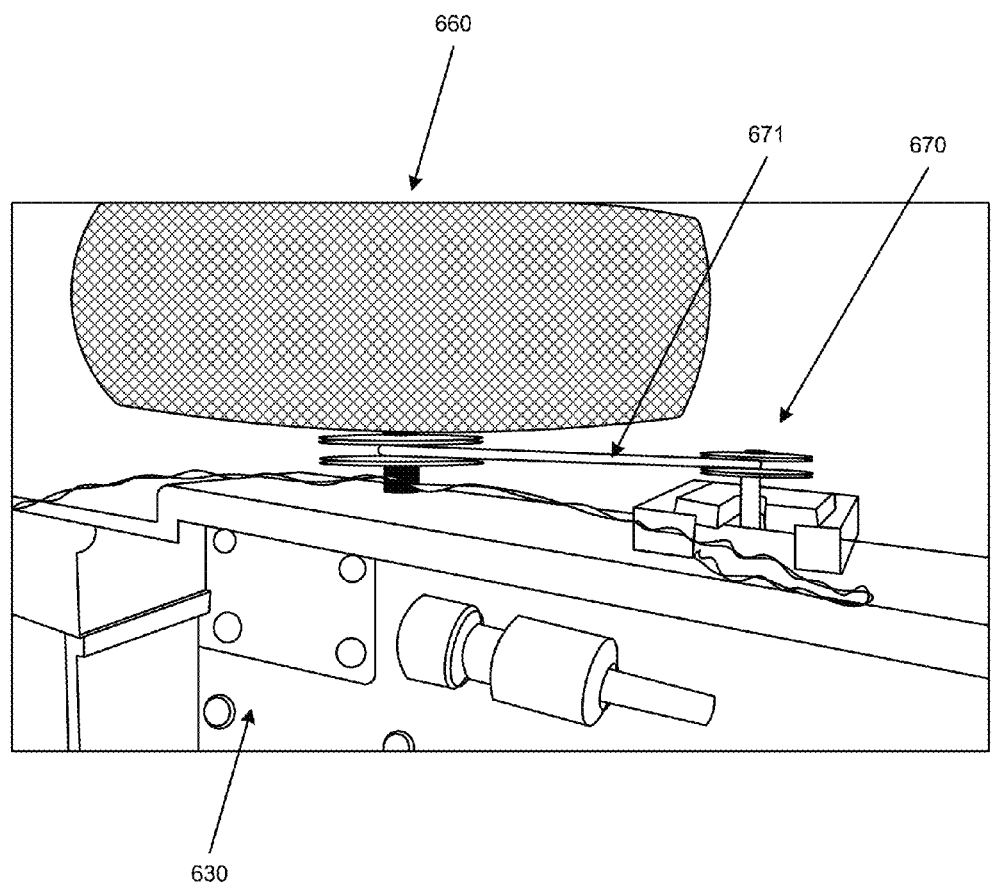
FIG. 6 is a diagram that illustrates at least a portion of a distance measurement system associated with a vehicle.

FIG. 6 is a diagram that illustrates at least a portion of a distance measurement system 670 associated with a vehicle 630. The distance measurement system 670 is mechanically coupled to at least a portion of a movement mechanism 660. Specifically, the distance measurement system 670 is coupled via a pulley 671 (e.g., a belt system) attached to an axle (e.g., rear axle, a main axle) included in the movement mechanism 660 (and/or a probe).

Referring back to FIG. 1, the system 100 can include a location tracking system 120. The location tracking system 120 can be configured to collect data (e.g., location data) identifying or representing a location of the system 100 with respect to time. Accordingly, test data (e.g., impedance data) that are collected using the probe 105 can be correlated to a location and/or a time. In some implementations, location data collected by the location tracking system 120 can be correlated with (used in conjunction with) distance data from the distance measurement system 170.

In some implementations, the location tracking system 120 can include, or can be, a global positing system (GPS) system (e.g., a differential GPS system (also can be referred to as a differential location tracking system)). A differential GPS system can enable, for example, cm-level resolution between the data acquisition system location tracking (e.g., a GPS) receiver and a base station (not shown in FIG. 1). A differential location tracking system can be used to rapidly capture test data that can be location-referenced.

In some implementations, a real-time cm-level location tracking system implemented by the location tracking system 120 can be used for rapid test data collection and accurate correlation of the test data collected using the probe 105 with the actual sampling locations produced using the location tracking system 120. Accordingly, test data difficulties can be made obsolete through this technology. A variety of real-time kinematic (RTK) location (e.g., GPS) tracking and other location tracking (e.g., GPS) solutions can be used in the location tracking system 120. In some implementations, the location tracking system 120 can include an antenna (on a metal shield to ensure that a ground-reflected signal may not interfere with satellite measurements).

In some implementations, using the location tracking system 120, test data acquired can have a real-time timestamp from a satellite as well as accurate positioning. In some implementations, the computing device 110 can be configured to map the movement of the system 100 and plot it in real-time for users to be able to use to make decisions about which areas (on a surface) should be interrogated (or interrogated again), which areas are missed, possible problems (such as ground disconnections) that may have arisen during the interrogation, and/or so forth. In some implementations, the test data can be stored in a memory of a computing device. More details related to mapping of test data are described below.

Referring back to FIG. 1, and as mentioned above, a fluid can be used in conjunction with the system to, for example, wet a surface 10 and/or the probe 105 to facilitate interrogation. The system 100 includes a fluid management system 140 configured to provide a fluid that can be used by the system 100 during interrogation. The fluid management system 140 can be configured to provide a film of fluid for electrical conductivity between the electrical elements of the probe 105 (e.g., rotating members, rolling devices or probes, coupled thereto) and/or the elements of the probe 105 (e.g., the rotating members themselves) and the surface 10 (e.g., concrete) for more accurate measurements. The fluid management system 140 can provide electrical connection (e.g., desirable electrical connection) with the surface 10. In some implementations, the system 100 can be configured so that a single operator can both apply a fluid (e.g., conductive fluid) to the surface 10 (e.g., a bridge surface) while interrogating the surface 10 without an additional operator.

In some implementations, the fluid management system 140 can include at least a portion that can be moved between a deployed configuration and a stowed configuration. In some implementations, a portion of the fluid management system 140 can be a fluid distribution system. A portion of the fluid management system can be configured to distribute fluid in the deployed configuration and in the stowed configuration. In some implementations, a portion of the fluid management system 140 can be moved to the deployed configuration to provide a fluid to at least a portion of the probe 105 and/or the surface 10. Accordingly, a portion of the fluid management system 140 can be positioned to provide the fluid to at least a portion of the probe 105 and/or the surface 10. In some implementations, a portion of the fluid management system 140 can be moved to the stowed configuration when not providing a fluid to at least a portion of the probe 105 and/or the surface 10.

In some implementations, the fluid management system 140 can be configured to moisten the probe 105 and/or the surface 10 with a fluid (e.g., a conductive solution) prior to testing and/or maintain the probe 105 and/or the surface 10 in a moist state during testing, through piping of the fluid from a reservoir (not shown) included in the fluid management system 140. The fluid management system 140 can also include a pump (or pump system) (not shown in FIG. 1) configured to move the fluid from the reservoir (not shown in FIG. 1) to desirable locations during testing. The reservoir of the fluid management system 140 can be placed on the vehicle 130 or carried in some other way to at least some portion of the probe 105 and/or the surface 10. In some implementations, the reservoir can be, or can include, an interchangeable bucket system that can allow for rapid swapping of buckets of a fluid (e.g., a conductive fluid). The reservoir can also include a valve system (not shown in FIG. 1) that can be used to control fluid flow.

In some implementations, the fluid management system 140 can be configured to provide a fluid to (e.g., directly to) one or more portions of the probe 105 before, after, and/or during interrogation of the surface 10. For example, in some implementations, the fluid management system 140 can be configured to provide a fluid to one or more rotating members included in the probe 105 such as the rotating members 207 shown in FIGS. 2A and 2B, the rotating members 307 shown in FIG. 3, and/or so forth.

As a specific example with reference to FIG. 3, in some implementations, one or more fluids can be injected through or onto one or more of the rotating members 307 (e.g., two of the rotating members 307 toward a front of a vehicle in the direction that the vehicle is moving) as the probe 305 is rolling on a surface. The one or more fluids can be injected through or onto the one or more of the rotating members 307 through or around the support 309.

In some implementations, the fluid management system 140 can be configured to provide a fluid to (e.g., directly to) one or more portions of the surface 10 (and/or probe 105) before, after, and/or during interrogation of the surface 10. In some implementations, the fluid management system 140 can be configured provide a fluid to the surface 10 (and/or the probe 105) using a fluid distribution system that can include, for example, a sprayer. The fluid distribution system can be configured to provide a fluid at a location distal to the system 100 (in front of the system 100 at location to which the system 100 is being moved).

Figure 7A:
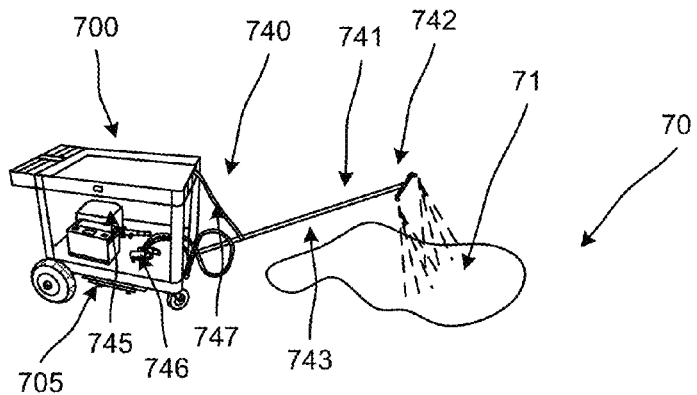
FIGS. 7A and 7B illustrate an example of fluid management system included in a system that includes a fluid distribution system configured to provide a fluid to a surface.
Figure 7B:
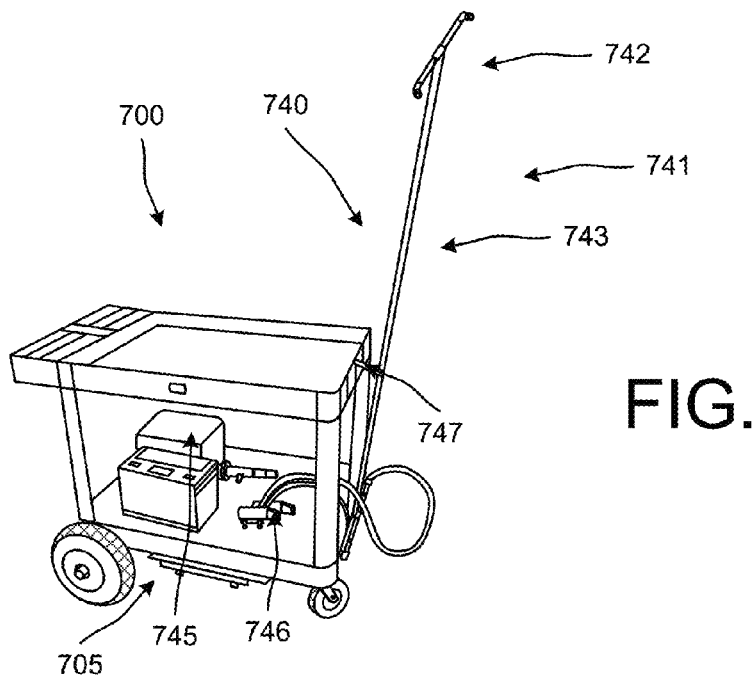

FIGS. 7A and 7B illustrate an example of fluid management system 740 included in a system 700 that includes a fluid distribution system 741 configured to provide a fluid 71 to a surface 70. The fluid distribution system 741 includes a fluid reservoir 745, a pump system 746, and at least one sprayer 742 in fluid communication with a lumen 743 defined by a pipe. As shown in FIG. 7A, a wet area 71 in front of (e.g., distal to) the system 700 and probe 705 is sprayed using the fluid distribution system 741. The fluid distribution system 741 is illustrated in FIG. 7A in a deployed configuration. FIG. 7B illustrates the fluid distribution system 741 in a stowed configuration. The fluid distribution system 741 can be hingedly coupled to the system 700 so that the fluid distribution system 741 can be moved between the stowed configuration and the deployed configuration.

In some implementations, a mechanism (as part of the fluid management system 740) can be used to maintain and or move the fluid distribution system 741 between the stowed configuration and the deployed configuration. In some implementations, the mechanism can include a motor, a latch, a strap (shown in FIGS. 7A and 7B as element 747), a pulley, and/or so forth.

In some implementations, when in a stowed configuration, the fluid management system 740 can be moved into, for example, a building or a laboratory. In other words, the fluid management system 740 can be folded so that the fluid management system 740 and system 700 can be moved through a relatively tight space such as a doorway (e.g., vehicle doorway) and/or other storage space. In some implementations, the fluid management system 740 can be removably coupled to (e.g., coupled to and decoupled from) the system 700.

Figure 7C:
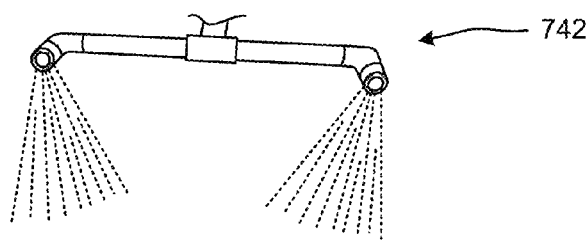
FIG. 7C illustrates a view of a sprayer shown in FIGS. 7A and 7B.

FIG. 7C illustrates a view of the sprayer 742 shown in FIGS. 7A and 7B. In some implementations, the sprayer can be configured with a fluid distribution profile (e.g., a flow rate, a flow pattern, a flow angle, and/or so forth) that can be adjusted. In some implementations, the sprayer 742 can be a sprayer configured to adjust the fluid distribution profile in response to movement (e.g., a speed, a direction) of the system 700. In this implementation, the sprayer 742 includes two sprayer heads. In some implementations, different types and/or numbers of sprayers and/or sprayer heads can be included in the fluid distribution system 741.

Referring back to FIG. 1, the system 100 can include a marking system 180. The marking system 180 can be configured to apply a mark (e.g., a painted dot, a marker) to the surface that can be used to reference one or more locations on the surface 10 (e.g., bridge) for subsequent association of test data to location. In some implementations, test data can be acquired from one location to another location as the data acquisition system 100 is moved (e.g., rolled), and the marking system 180 can be configured to apply one or more marks to the surface 10 so that impedance information can be associated with a particular point on the surface 10 (e.g., bridge).

Manually marking the surface 10 (e.g., a deck or pavement layer) can be time-consuming. Accordingly, eliminating manual marking may be desirable. In an example implementation, the system 100 can be configured to perform automatic marking using the marking system 180. For example, at least one trigger criterion (e.g., a threshold value for a spatial variation) can be established that causes automatic marking should the trigger criterion (or condition) be satisfied (e.g., met).

In some implementations, marking can be performed using the marking system 180 incorporated into the system 100 concurrent (e.g., during, coincident) with testing of an area. For example, the marking system 180 could be mounted in or on the system 100. As such, the collected test data may be evaluated and the marking system 100 triggered to mark based on the trigger criterion before the marking system 180 (or system 100) moves beyond the location (or moves beyond a threshold distance) on the surface 10 from which the test data are collected.

In some implementations, marking can be performed using the marking system 180 (e.g., the marking system 180 incorporated into the system 100 or a standalone marking system (not shown)) after testing of an area has been completed. For example, the system 100 can be configured to test a first area of the surface 10 and test a second area of the surface 10. After testing of the second area of the surface 10 has been completed, marking of the first area and the second area can commence using the marking system 180 (or a standalone marking system 180) of the system 100.

Test data can be collected, and then (at a later time) the marking system 180 (or standalone marking system) can rely on pre-prepared location-referenced test data rather than active measurements. For example, this configuration may be appropriate when the system 100 moistens the surface 10 to a point that marking the surface is undesirable (until drying occurs). For example, this configuration may be appropriate when trigger criteria cannot be developed until after the collected test data are interpreted at a remote location, for example. Being able to deploy a marking system independent of other testing devices could then be advantageous because only a marking system would be transported back to a surface for marking, and the test data collection components (including a probe) could be deployed elsewhere. In this case, the marking system could be configured with a location tracking feature (e.g., a distance measurement instrument, a global positioning system, or another similar system).

Figure 8:
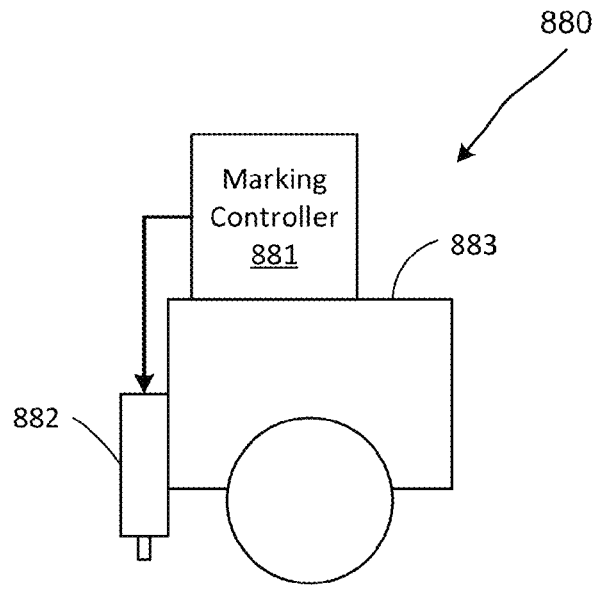
FIG. 8 illustrates a block diagram of a marking system according to at least one example implementation.

FIG. 8 illustrates a block diagram of a marking system 880 according to at least one example implementation. The marking system 880 can be a standalone marking system (separate from a probe or other testing device) or can be incorporated into (e.g., coupled to, coupled to using a hitch) a data acquisition system (e.g., system 100 shown in FIG. 1). As shown in FIG. 8, the marking system 880 includes a marking controller 881, a marking apparatus 882, and a vehicle 883. The vehicle 883 can be any type of vehicle discussed above.

Referring back to FIG. 1, the computing device 110 of the system 100 can be configured to evaluate incoming test data and compare the test data to a trigger criterion or set of trigger criteria. In some implementations, the trigger criteria can be based on, for example, impedance values, location, size (e.g., surface area), and/or so forth. The computing device 110 can be configured to signal (e.g., cause a signal to be transmitted) to the marking system 180 at a location from which the test data were collected upon determining that the test data meets the criterion or criteria (e.g., exceeds, matches or is less than a threshold value(s)). For example, the computing device 110 can include a testing controller (not shown) that can include a processing module configured to cause (e.g., trigger) the testing controller to signal the marking system 180 to mark a defect on tested pavement should the tested pavement include a defect (e.g., based on the trigger criterion or criteria).

Accuracy in the automatic marking system could be ensured, for example, through a location tracking system 120 on the system 100 and/or information about the relative locations of the probe 105 and the marking system 180 on the system 100. The location tracking system 120 can, in some implementations, be a distance measurement instrument, a global positioning system, or another similar system.

Referring back to FIG. 8, in an example implementation, the marking apparatus 882 can include, or can be, an electrically activated mechanical system (e.g., an electrically activated dispensing system, an electrically activated mechanical system for spraying paint). For example, if including a paint spraying system, the paint can be in a standard upside-down spray can used for utility marking. Alternatively, the paint can be in a different kind of container and/or dispensed in a fashion other than spraying (writing with a paint pen, launching paintball markers, etc.). A marking material other than paint can also be used (e.g., ink, dye, chalk, and/or the like). In some implementations, marking apparatus 882 can be configured to dispense a marker (e.g., a pin, a plastic marker).

In some implementations, a marker (e.g., paint or other marking material) may have characteristics including being electrically conductive, magnetic, washable, visible only in certain conditions (e.g., when viewed under infrared or fluorescent light), and/or so forth. In other words, using a paint with special characteristics can include making the paint invisible under natural conditions, which may ensure that drivers (e.g., on a bridge or roadway) would not be confused by the additional markings.

In some implementations, multiple markers (e.g., paint), colors, patterns, and/or intensities can be utilized. For example, each color, pattern, and/or intensity could correspond to a particular trigger criterion. Accordingly, multiple levels of a given property and/or multiple types of properties could be indicated on a surface 100. The multiple levels of a given property and/or multiple types of properties could be marked on a surface simultaneously for devices that have the ability to simultaneously (or non-simultaneously) make such measurements. In addition, the marking system 880 could be configured to mark a center or middle of an area of interest (e.g., concern) or to mark an edge or boundary of an area of interest.

Figure 9:
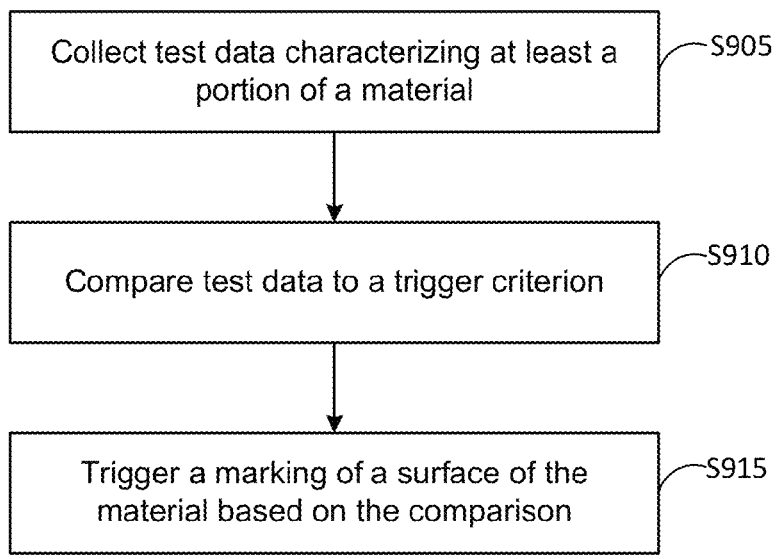
FIG. 9 illustrates a method of operating a surface marking system according to at least one example implementation.

FIG. 9 illustrates a method of operating a surface marking system according to at least one example implementation. At S905, test data characterizing at least a portion of a material (e.g., pavement or concrete) can be collected. The test data can be collected using a test method (e.g., non-destructive test method) as described above. At S910, the test data can be compared to a trigger criterion (or condition). At S915, a marking of a surface of the material can be triggered based on the comparison.

Referring back to FIG. 1, in some implementations, the system 100 can include a multi-channel measurement system in the computing device 110, and the marking system 180 can also include multiple channels that correspond with the multi-channel measurement system. Whether the data collection apparatus and marking system are mounted on the same vehicle (e.g., platform) or deployed independently, a marking channel could be assigned to each test data collection channel (or to output from the given test data collection channel provided in the form of a map or other location-referenced data), or various automatic marking channels could be assigned to various data collection channels as needed to accomplish the project objectives. In this arrangement, the marking channels may share one or more reservoirs of markers (e.g., paint), or they may each have their own reservoir or reservoirs of markers (e.g., paint).

Figure 10:
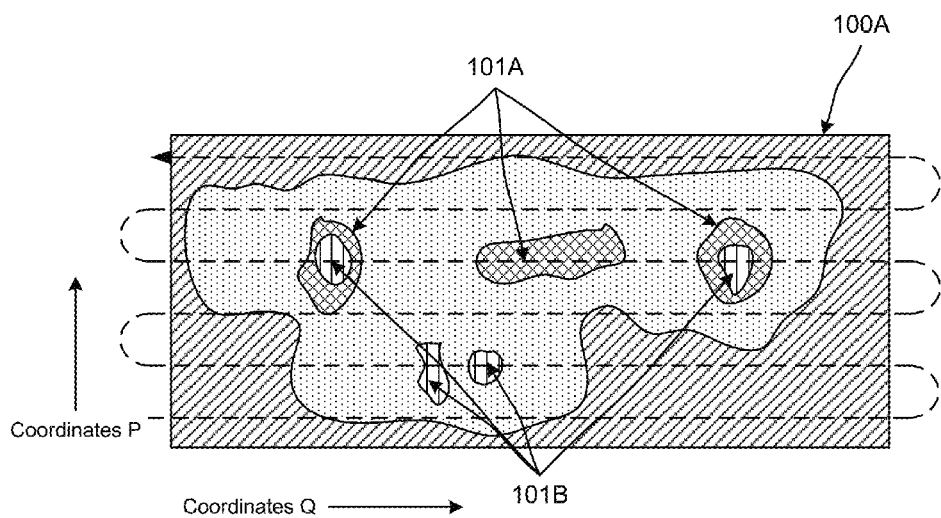
FIG. 10 illustrates a test data map of an area according to an implementation.

FIG. 10 illustrates a test data map of an area 100A according to an implementation. The test data map corresponding to area 100A can be produced using the computing device 110 of the system 100 shown in FIG. 1. The area 100A is shown in this implementation as a rectangular area, but an area having a different shape can be interrogated in some implementations. The test data map can, in some implementations, be produced in real-time using the computing device 110 of the system 100. In some implementations, real-time information can be used by an operator as feedback about the test data being collected as it is being collected by the system 100.

As shown in FIG. 10, different impedance measurements are plotted along coordinates Q and P. The location data in Q and P coordinates used to define the test data map can be acquired and/or produced using the location tracking system 120 and/or the distance measurement system 170 of the system 100 in conjunction with test collected using the probe 105 and computing device 110. The different regions (or areas) in the two-dimensional map represent different impedance values. For example, the regions that are crossed-hatched (101A) can represent a first impedance value, and the regions with vertical lines (101B) can correspond with a second impedance value. The dashed lines through the area represent a scan path of the system 100 through the area 100A. In some implementations, the system 100 (e.g., using the marking system 180) can be configured to mark one or more regions depending on the trigger criteria associated with, for example, impedance values, size, location, and/or so forth.

In some implementations, relatively low impedance regions can be tested and can be associated with lower quality asphalt or concrete cover, for example. These results can be confirmed by core samples. In some implementations, a particular scan path can take as little as a few minutes to move along with an operator spraying a surface (e.g., concrete) in front of (e.g., in front of a direction of movement of) the system 100 using an apparatus (e.g., a hand-held sprayer or fluid distribution system with, for example, a soap and water solution).

In some implementations, a variety of test data maps can be produced. For example, test data based on a logarithmic scale can be included in the test data map. In some implementations, test data maps including color coding, three-dimensional features, and/or so forth can be produced using the computing device 110.

Figure 11A:
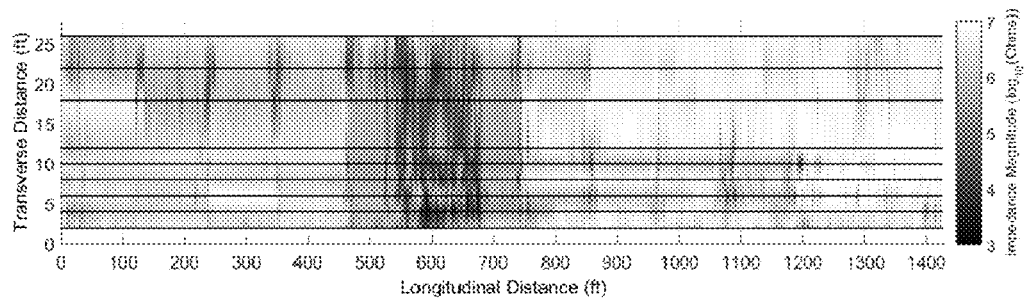
FIGS. 11A and 11B illustrate other types of graphs that can be produced.
Figure 11B:
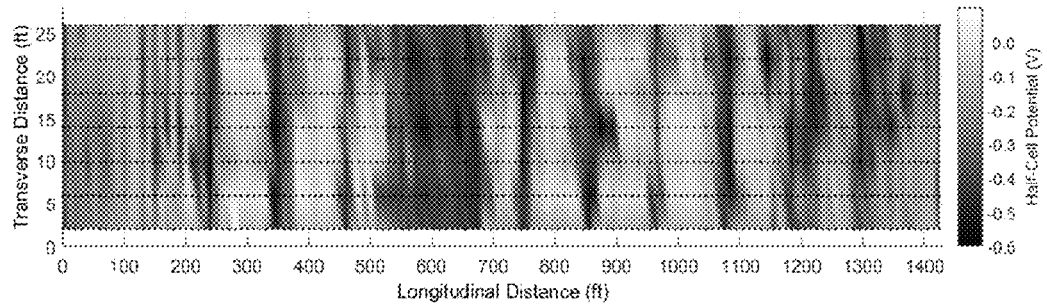

FIGS. 11A and 11B illustrate other types of graphs that can be produced using the computing device 110 of the system 100. As shown in FIG. 11A, example test data collected from a surface (e.g., a bridge surface) measuring 1425 feet long includes impedance test data recorded over four orders of magnitude. When compared with half-cell potential data in FIG. 11B, the relationship between concrete cover protection and corrosion can be determined.

FIG. 11A illustrates impedance data mapped according to longitudinal distance. The lines in FIG. 11A illustrate paths of the data acquisition system during measurements.

FIG. 11B illustrates half-cell potential data. As illustrated in FIG. 11B, the low half-cell portions around 600 ft are associated with concrete that is more electrically conductive as shown in FIG. 11A.

Ultimately, one or more maps (and/or graphs) could be generated from the impedance test data and/or referenced to particular locations along the surface that is interrogated. For example, a map of impedance test data is shown in at least FIG. 11A and described above. Test data, along with statistics of the percentage of surfaces (e.g., decks) that have relatively high or low impedance, can be useful to, for example, infrastructure managers to program and prioritize rehabilitation efforts.

The maps illustrated in FIGS. 11A and 11B demonstrate the utility and/or speed of the impedance measurement system within a data acquisition system employing rolling probe and spraying mechanisms. In some implementations, starting and stopping positions along a surface may be noted.

In some implementations, to perform a half-cell potential test or other type of impedance measurement on a surface, connection to a metal reinforcement (rebar) below the surface to establish an electrical circuit may be needed. That connection can function as a voltage reference for one or more other measurements. In the system 100 including a fixed and/or a rotating member within a probe, electrical connection can be a step in a measurement method.

This direct physical connection (e.g., tethering) to the rebar can be challenging for many reasons. In some implementations, direct physical connection may require prior knowledge of the location of the rebar. In some implementations, making a connection may require a destructive process for exposing the rebar, which not only takes time but also generally involves heavy equipment or machinery. In some implementations, a direct electrical connection to the rebar may be possible by drilling a hole into the rebar, tapping it, and then installing a screw into the hole. In some implementations, a conductive adhesive may be used. In some implementations, a cord may be pinned against the exposed rebar with a heavy object (e.g., metal rod), and a conductive fluid may be poured into or placed at the interface between the cord and the rebar. In some implementations, the connection can be made to be robust (in response to being pulled by a force). In some implementations, a cord to this grounded connection may be moved to whatever apparatus is making the electrical measurement. In some implementations, a repair may be made to the exposed rebar to prevent further deterioration at that point and to prevent any road hazards. In some implementations, it may be a challenging process to establish the necessary electrical connection for many tests. In some implementations, depending on the electrical continuity of the surface (e.g., bridge surface), especially if the surface has multiple spans, multiple electrical reference points may need to be established.

In some implementations, the tethered approach to providing a voltage reference can inhibit a technician or researcher from making a rapid measurement on a bridge deck using electrical methods that require this type of reference. In some implementations, a method can be used to overcome limitations of direct grounding to allow at least for more rapid scanning of, for example, a bridge deck using impedance and/or voltage sensing methods.

In some implementations, a relatively large area of a ground (also can be referred to as a potential) reference electrode (which is not a guard ring in some implementations) is substantially larger than that of an active electrode (which is also surrounded by a guard ring in some implementations or which is not surrounded by a guard ring in some implementations). Some implementations of the relative geometry of this configuration are shown in FIG. 12.

Figure 12:
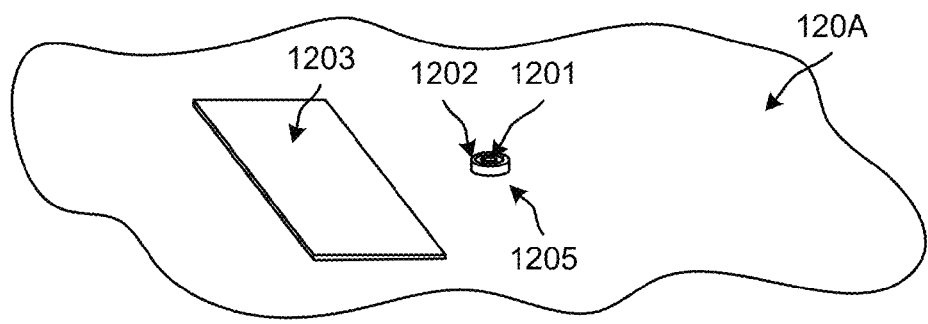
FIG. 12 illustrates a probe and a ground reference electrode on top of a surface.

FIG. 12 illustrates a probe 1205 and a ground reference electrode 1203 on top of a surface 120A. The probe 1205 includes an interior electrode 1201 (e.g., interior rotating member(s)) and a guard ring 1202 (e.g., exterior rotating member(s)). The ground reference electrode 1203 also can be referred to as a large ground reference electrode or as a large conductor. In some implementations, the probe 1205 and/or the ground reference electrode 1203 can have a different shape or profile (e.g., different thickness, non-rectangular, curved, triangular, etc.) than shown in FIG. 12.

In some implementations, the ground reference electrode 1203 can be much larger than the probe 1205. The ground reference electrode 1203 can have a surface area at least two times (e.g., 3 times, 4, times, 5 times, 10 times, 100 times) greater than a surface area occupied by the probe 1205. For example, the ground reference electrode 1203 (which can include multiple portions) can have a surface area (e.g., a combined surface area) of at least a square meter, and the probe 1205 can have a surface area at least two times less than the square meter. In some implementations, having a difference of ten (10) times can be critical to operation to obtain a desirable localization of the impedance measurement of the surface (e.g., concrete surface) below the probe 1205 (e.g., inside the perimeter 208 defined in FIG. 2A).

In some implementations, rotating members can be included in the probe 1205 and/or the ground reference electrode 1203 can be configured to rotate about one or more axes that can be aligned parallel to one another. In some implementations, the probe 1205 and/or the ground reference electrode 1203 can exclude a rotating member. An example of a static probe is discussed at least in connection with FIGS. 15A and 15B.

A wire between the ground reference electrode 1203 and rebar (not shown in FIG. 12) is eliminated such that a direct electrical connection (e.g., via a wire or other conductor) between the ground reference electrode 1203 and rebar is excluded. Accordingly, the ground reference electrode 1203 can be moved with the probe 1205 (because the ground reference electrode 1203 is not tethered via a wire). The ground reference electrode 1203, which is substantially greater in surface area than the probe 1205, can be used in place of a direct rebar connection. In some implementations, the ground reference electrode 1203 can be made of a conductive material such as steel, aluminum, etc.

Figure 13:
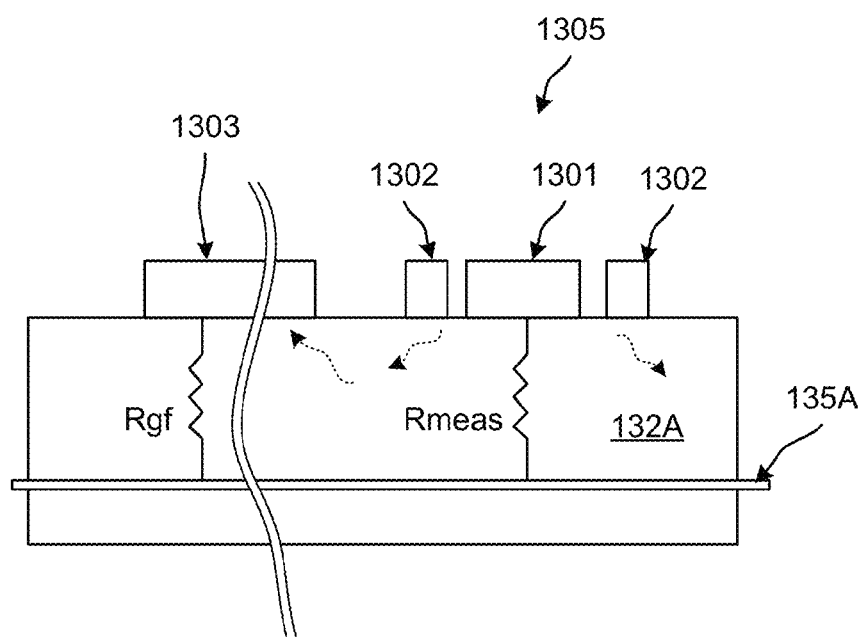
FIG. 13 is a diagram that illustrates resistances associated with a ground reference electrode and probe.

FIG. 13 is a diagram that illustrates that a resistance Rgf to the ground reference electrode 1303 is less than (e.g., much less than) the desired measured resistance Rmeas from the probe 1305 because of the large area of the ground reference electrode 1303 relative to the active or interior electrode 1301 of the probe 1305. In this implementation, the guard ring 1302 may be used so that stray currents (represented by wavy arrows) are not measured as part of the current going into the active or interior electrode 1301.

Accordingly, the resistance Rgf from the rebar 135A through the material 132A (e.g., concrete) to the ground reference electrode 1303 can be much smaller than that of the resistance Rmeas of the active or interior electrode 1301 to the rebar 135A as shown in FIG. 13.

Table 1 below illustrates that the current measured through the center of the interior electrode 1301 is changed by a relatively small amount by using a ground reference electrode 1303. In this implementation, the guard ring 1302 and the interior electrode 1301 are at a constant potential of 1 V. In this implementation, the ground reference electrode 1303 floats in one simulation while a rebar mat is forced to a potential of 0 V. In other implementations, the rebar mat is allowed to float while the ground reference electrode 1303 is forced to a potential of 0 V. In this implementation, the relative influence can be calculated in each of these cases. In this implementation, the current density through the interior electrode 1301 can be measured.

TABLE 1

| Resistivity of Concrete (Ohm-m) | Ground reference electrode potential (V) | Rebar potential (V) | Measured current density through active circular electrode (A/cm²) |
|---|---|---|---|
| 40 | $1.3 \times 10^{-7}$ (floating) | 0 | $9.79 \times 10^{-8}$ |
| 40 | 0 | $3.0 \times 10^{-2}$ (floating) | $9.51 \times 10^{-8}$ |
| 4 | $1.3 \times 10^{-7}$ (floating) | 0 | $9.62 \times 10^{-7}$ |
| 4 | 0 | $3.0 \times 10^{-2}$ (floating) | $9.33 \times 10^{-7}$ |
| 0.4 | $1.3 \times 10^{-7}$ (floating) | 0 | $9.66 \times 10^{-6}$ |
| 0.4 | 0 | $3.0 \times 10^{-2}$ (floating) | $9.37 \times 10^{-6}$ |
| 0.04 | $1.4 \times 10^{-7}$ (floating) | 0 | $9.66 \times 10^{-5}$ |
| 0.04 | 0 | $3.1 \times 10^{-2}$ (floating) | $9.37 \times 10^{-5}$ |

As shown Table 1, a relative influence of leaving the rebar floating and using the ground reference electrode 1303 is shown. In some implementations, the measured current density can scale appropriately with increasing concrete resistivity and on an order of magnitude level. The difference in the measured current density can be relatively small for the case where the ground reference electrode 1303 potential of 0 V is used and the rebar is allowed to float.

In some implementations, this can indicate that, for impedance measurements of the concrete, connecting to the rebar only slightly changes the relative measure of the current density through the interior electrode 1301. These results indicate that the ground reference electrode 1303 can be used in place of a direct rebar connection.

Figure 14:
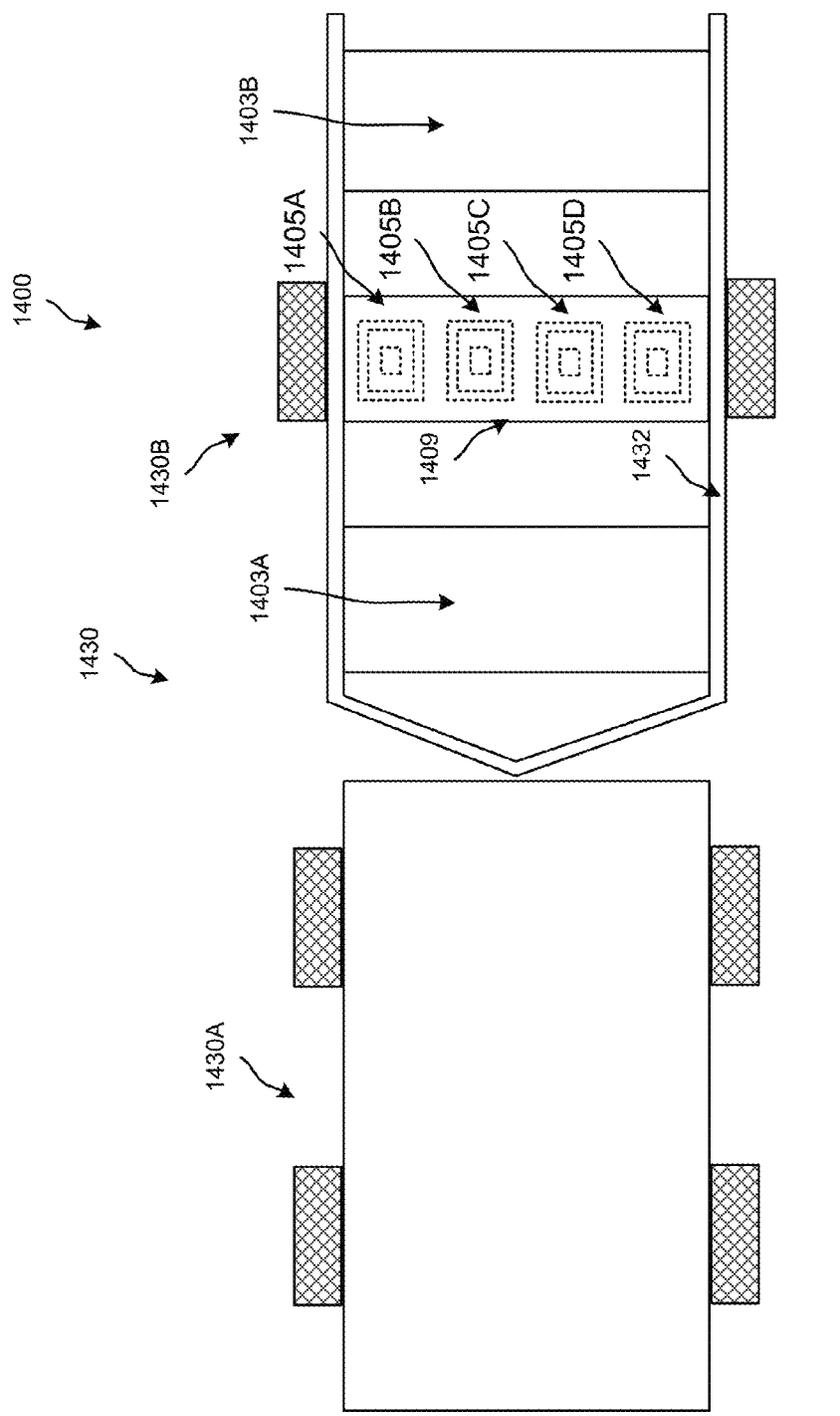
FIG. 14 is a diagram that illustrates another implementation of a data acquisition system.

While in some implementations a static system can include a single large electrode and smaller guarded active electrode that is moved around, a vehicle 1430 configuration that allows for measurement of multiple channels of impedance test data during a single pass over a surface (e.g., a bridge surface) is shown in at least FIG. 14 (which is a variation of the system 100 shown in FIG. 1). Although not explicitly shown, any of the elements and/or features shown and described in connection with FIG. 1 (or any of the other figures) can be incorporated into the variation illustrated in FIG. 14.

As shown in FIG. 14 (which is a top view of a system 1400), multiple ground reference electrodes 1403A, 1403B, or additional electrodes, can be included in the system 1400. In this implementation, probes 1405A through 1405D (which each include at least one interior electrode (which can be an active electrode) and at least one exterior electrode (defining a guard ring)) are disposed (e.g., disposed laterally) between the ground reference electrode 1403A and the ground reference electrode 1403B. The ground reference electrode in front of (e.g., 1403A) and behind (e.g., 1403B) the probes 1405A through 1405D can ensure a desirable connection at the beginning and end of a run or over any discontinuities that may exist between different spans along a surface. This can also be useful for, for example, parking lots or other structures having edges of materials (e.g., joints), where electrical continuity is not guaranteed, that will need to be spanned.

Although not explicitly shown in FIG. 14, one or more of the ground reference electrodes 1403A, 1403B can be, or can include (or exclude in some implementations), one or more rotating members. These rotating members can be similar to, or the same as, the rotating members and associated mechanisms (e.g., lift mechanisms, supports, etc.) described above with respect to the probes (e.g., probe 105 in FIG. 1). In some implementations, rotating members included in one or more of the probes 1405A through 1405D and/or one or more of the ground reference electrodes 1403A, 1403B can be configured to rotate about one or more axes that can be aligned parallel to one another (and/or parallel to one or more axes of the vehicle 1430).

In some implementations, the vehicle 1430 can be or can include, for example, a motorized vehicle 1430A (e.g., truck) pulling a trailer 1430B (which includes the ground reference electrodes 1403A, 1403B and the probes 1405A through 1405D). In some implementations, the trailer 1430B can include a hitch so that the trailer 1430B can be removably coupled to the motorized vehicle 1430A. The ground reference electrodes 1403A, 1403B and probes 1405A through 1405D can be operably coupled to a frame 1432 of the trailer 1430B. The probes 1405A through 1405D are illustrated with dashed lines because they can be disposed below a support 1409 used to operably couple the probes 1405A through 1405D to the trailer 1430B. Although not shown, in some implementations, multiple probes and ground reference electrodes can be incorporated into a vehicle. The cross-hatched objects illustrated in FIG. 14 can represent wheels included in a movement mechanism.

In some implementations, although a computing device is not illustrated in FIG. 14, the probes 1405A through 1405D can be controlled independently and/or can be used with a variety of waveforms (particularly, at different frequencies that can be included in or associated with a computing device) to interrogate the impedance properties of the surface over which the system 1400 scanning.

In the configuration shown in FIG. 14, fluids to enhance conductivity (which can include water and/or detergent) may be used in a relatively large volume for a surface to be interrogated. In some implementations, the vehicle 1430 can include a marking system, a distant measurement system, a location tracking system, a fluid management system, and/or so forth. In some implementations, a conductive solution can be applied from the front (e.g., left side in FIG. 14) of the motorized vehicle 1430A to allow for sufficient time for a fluid to soak into a surface (e.g., a concrete surface or other porous surface) and/or wet a non-porous surface as the system 1400 moves along direction X1. In some implementations, a distance measurement system can be included in, for example, an axle of the trailer 1430B (and/or motorized vehicle 1430A) with an angle encoder used to estimate distance traveled.

Figure 15A:
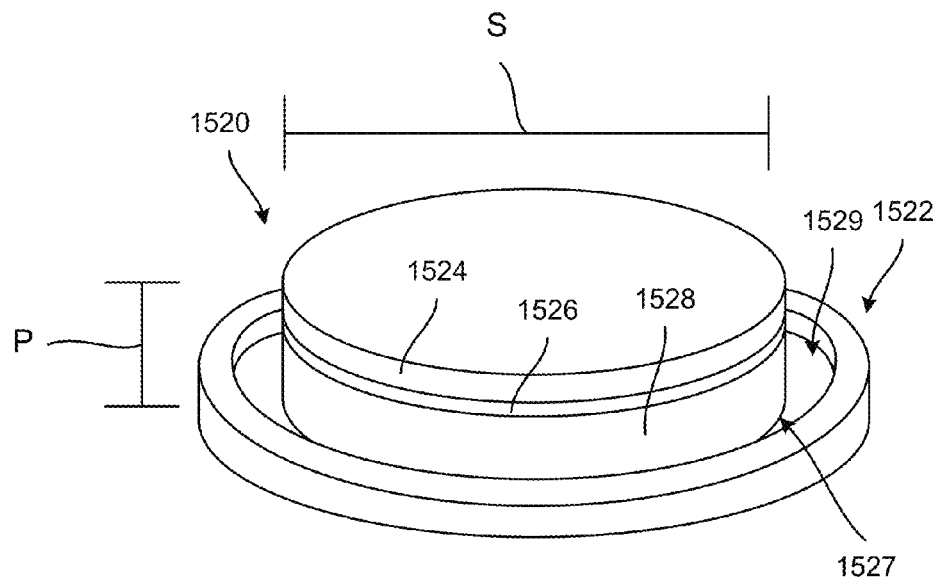
FIGS. 15A and 15B are diagrams that illustrate a probe and a guard ring.
Figure 15B:
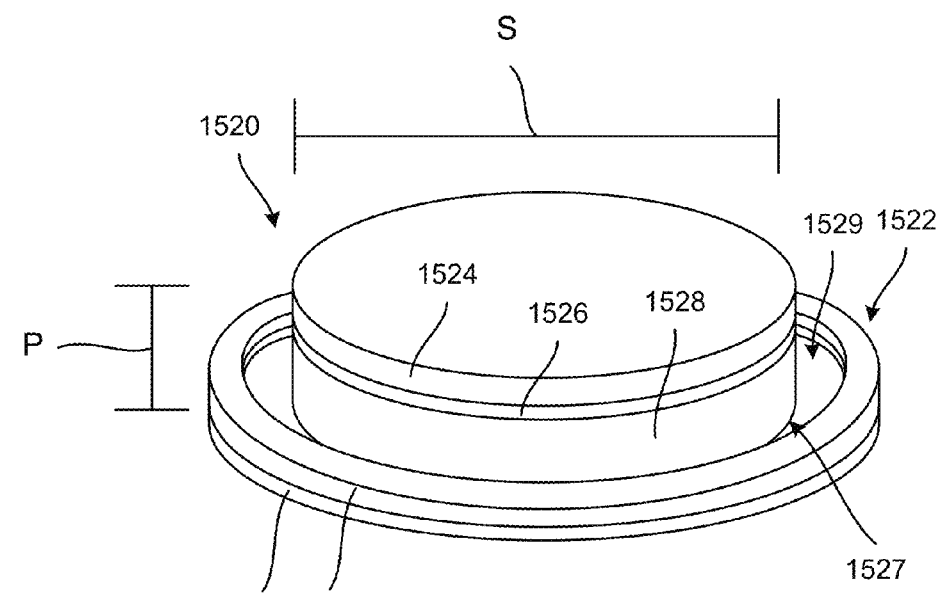

FIGS. 15A and 15B are diagrams that illustrate a probe 1520 and a guard ring 1522, according to an implementation. As shown in FIGS. 15A and 15B, the probe 1520 includes multiple layers of material. Specifically, the probe 1520 includes a conductive portion 1526 disposed between a fluid retention portion 1528 and a support portion 1524. The conductive portion 1526 can be made of a variety of conductive materials such as aluminum, copper, steel wool, stainless steel, a conductive epoxy, and/or so forth. The fluid retention portion 1528 can be made of any type of material that can be configured to retain a conductive fluid such as an ionic solution (e.g., a solution with a detergent, a salt solution). In some implementations, the fluid retention portion 1528 can be made of, for example, a foam, (e.g., Styrofoam (e.g., compressible Styrofoam)), wood, a sponge (e.g., a stiff sponge), and so forth. The guard ring 1522 can be made of a variety of conductive materials such as aluminum, copper, steel wool, stainless steel, and/or so forth. In some implementations, the guard ring 1522 can have the same layers (e.g., conductive portion, support portion, fluid retention portion) or different layers than the probe 1520. For example, as shown in FIG. 15B, the guard ring 1522 includes a fluid retention portion 1521 and a conductive portion 1523. Although not shown in FIG. 15B, the guard ring 1522 can also include a support portion. Referring back to FIGS. 15A and 15B, in some implementations, the support portion 1524 can be made of, for example, a plastic material, an insulating material, and/or so forth. In some implementations, the support portion 1524 may be optionally omitted from the probe 1520. In some implementations, the components in the probe 1520 (interior portion, guard ring 1522, and/or gap) can each have a bottom surface aligned along a same plane.

In some implementations, the probe 1520 can include layers in addition to those shown in FIGS. 15A and 15B. For example, in some implementations, the probe 1520 can include multiple conductive portions (or layers) and/or multiple fluid retention portions (or layers).

In some implementations, the fluid retention portion 1528 can have a bottom surface 1527 configured to contact a surface of a portion of concrete (not shown). In some implementations, the bottom surface 1527 of the fluid retention portion 1528 can be configured to conform, at least in part, to a surface of concrete. Accordingly, the fluid retention portion 1528 can be made of a flexible (or semi-flexible) material that can enable a relatively stable electrical contact between the probe 1520 and a concrete surface. In some implementations, the bottom surface 1527 of the fluid retention portion 1528 can be configured so that it is rigid and does not conform, at least in part, to a surface of concrete. In some implementations, the probe 1520 can be a compressible probe.

As shown in FIGS. 15A and 15B, a gap 1529 is between the guard ring 1522 and the probe 1520. In some implementations, the gap 1529 can be a fraction of a diameter S of the probe 1520. For example, the gap 1529 can be less than or equal to 1/10 of the diameter S of the probe 1520, or greater than 1/10 of the diameter S of the probe 1520. In some implementations, the gap 1529 between the guard ring 1522 and the probe 1520 can be uniform or can be non-uniform. In some implementations, the gap 1529 can extend between a top of the guard ring 1522 to a bottom surface of the guard ring 1522. In some implementations, one or more materials can be inserted in the gap 1529 between the guard ring 1522 and the probe 1520 to function as an insulator between the guard ring 1522 and the probe 1520.

As shown in FIGS. 15A and 15B, the probe 1520 has a circular shape or outer profile. The probe 1520 has the diameter S of approximately 15 centimeters (cm). In some implementations, the diameter S of the probe 1520 can be different than 15 cm. For example, the probe 1520 can have a diameter S of approximately 100 cm. In some implementations, the probe 1520 can have a diameter S greater than 100 cm or a diameter S less than or equal to 100 cm.

In some implementations, reinforcing bars within concrete can define a grid (or some other pattern). In some implementations, the probe 1520 can be configured with a footprint (e.g., bottom surface area) that spans multiple reinforcing bars. In other words, in some implementations, the probe 1520 can be configured with a footprint that is greater than a grid size defined by reinforcing bars installed within concrete. The probe 1520 can be configured to span multiple reinforcing bars so that current can more easily flow from the probe 1520 through the concrete to the reinforcing bars, which define a ground node relative to the probe 1520.

In some implementations, the footprint of the probe 1520 (e.g., the bottom surface 1527 of the probe 1520) can be approximately 100 cm$^2$. In some implementations, the footprint of the probe 1520 can be greater than 100 cm$^2$ or less than 100 cm$^2$.

In some implementations, the probe 1520 can have a variety of shapes. For example, the probe 1520 can have a square outer profile, a rectangular outer profile, an octagonal outer profile, and so forth. In some implementations, the bottom surface 1527 of the probe 1520 may not be flat (e.g., may be curved).

As shown in FIGS. 15A and 15B, probe 1520 has a thickness P. In some implementations, the thickness P of the probe 1520 can be several centimeters. For example, the probe 1520 can have a thickness P of approximately 5 cm. In some implementations, the probe 1520 can have a thickness P greater than 5 cm or a thickness P less than or equal to 5 cm.

In some implementations, one or more weight elements can be placed on, or included in, the probe 1520 to facilitate contact of the probe 1520 with the surface of the concrete. In other words, in some implementations, a weight element can be integrated into the probe 1520. In some implementations, other types of mechanical mechanisms can be used to facilitate contact of the probe 1520 with a concrete surface. For example, a mechanical clip or other type of relatively sticky substance can be used to facilitate relatively tight contact of the probe 1520 with the concrete surface.

The disclosed implementations are merely examples, which may be embodied in various forms. Therefore, specific structural and functional details disclosed herein are not to be interpreted as limiting, but merely as a basis for the claims and as a representative basis for teaching one skilled in the art to variously employ the implementations in virtually any appropriately detailed structure. Further, the terms and phrases used herein are not intended to be limiting, but to provide an understandable description of the implementations.

Implementations of the various techniques described herein may be implemented in digital electronic circuitry, or in computer hardware, firmware, software, or in combinations of them. Implementations may implemented as a computer program product (e.g., a computer program tangibly embodied in an information carrier, a machine-readable storage device, a computer-readable medium, a tangible computer-readable medium) for processing by, or to control the operation of, data processing apparatus (e.g., a programmable processor, a computer, or multiple computers). In some implementations, a tangible computer-readable storage medium can be configured to store instructions that, when executed, cause a processor to perform a process. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be processed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special-purpose logic circuitry (e.g., an FPGA (field programmable gate array) or an ASIC (application-specific integrated circuit)).

Processors suitable for the processing of a computer program include, by way of example, both general and special-purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data (e.g., magnetic, magneto-optical disks, or optical disks). Information carriers suitable for embodying computer program instructions and data include all forms of non-volatile memory, including by way of example semiconductor memory devices (e.g., EPROM, EEPROM) and flash memory devices; magnetic disks (e.g., internal hard disks or removable disks); magneto-optical disks; and CD-ROM and DVD-ROM disks. The processor and the memory may be supplemented by, or incorporated in, special-purpose logic circuitry.

To provide for interaction with a user, implementations may be implemented on a computer having a display device (e.g., a cathode ray tube (CRT), a light emitting diode (LED), or liquid crystal display (LCD) display device) for displaying information to the user and a keyboard and a pointing device (e.g., a mouse or a trackball), by which the user can provide input to the computer. Other kinds of devices can be used to provide for interaction with a user, as well; for example, feedback provided to the user can be any form of sensory feedback (e.g., visual feedback, auditory feedback, or tactile feedback), and input from the user can be received in any form, including acoustic, speech, or tactile input.

Implementations may be implemented in a computing system that includes a back-end component (e.g., as a data server), or that includes a middleware component (e.g., an application server), or that includes a front-end component (e.g., a client computer having a graphical user interface or a Web browser through which a user can interact with an implementation), or any combination of such back-end, middleware, or front-end components. Components may be interconnected by any form or medium of digital data communication (e.g., a communication network). Examples of communication networks include a local area network (LAN) and a wide area network (WAN) (e.g., the Internet).

It will also be understood that when an element, such as a layer, a region, or a substrate, is referred to as being on, connected to, electrically connected to, coupled to, or electrically coupled to another element, it may be directly on, connected, or coupled to the other element, or one or more intervening elements may be present. In contrast, when an element is referred to as being directly on, directly connected to, or directly coupled to another element or layer, there are no intervening elements or layers present. Although the terms directly on, directly connected to, or directly coupled to may not be used throughout the detailed description, elements that are shown as being directly on, directly connected, or directly coupled can be referred to as such. The claims of the application may be amended to recite exemplary relationships described in the specification or shown in the figures.

The terms "a" or "an," as used herein, are defined as one or more than one. The term "another," as used herein, is defined as at least a second or more. The terms "including" and/or "having," as used herein, are defined as comprising (i.e., open transition). The term "coupled" or "removeably coupled," as used herein, is defined as connected, although not necessarily directly and mechanically. Accordingly, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes, and equivalents will occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. An apparatus, comprising:
   a probe including:
      a plurality of exterior rotating members defining a guard ring, and
      an interior rotating member having a circular shape and disposed within at least a portion of a perimeter defined by the plurality of exterior rotating members; and a waveform generator electrically coupled to the guard ring and the interior rotating member.

2. The apparatus of claim 1, wherein the waveform generator is configured to trigger flow of a current to a portion of concrete via the interior rotating member and configured to reference a potential of a reinforcing bar embedded within the concrete the apparatus, further comprising:
a current detector configured to detect a magnitude of the current.

3. The apparatus of claim 1, wherein each of the plurality of exterior rotating members is configured to rotate about an axis parallel to an axis about which the interior rotating member is configured to rotate.

4. The apparatus of claim 1, where the plurality of exterior rotating members and the interior rotating member are rotatably coupled to a support.

5. The apparatus of claim 1, wherein the probe is coupled to a vehicle,
the apparatus further comprising:
a distance measurement system coupled to the vehicle and configured to measure a distance of movement of the vehicle.

6. The apparatus of claim 1, wherein the probe is coupled to a vehicle,
the apparatus further comprising:
a fluid management system coupled to the vehicle and configured to dispense a fluid.

7. The apparatus of claim 1, wherein the probe is coupled to a vehicle,
the apparatus further comprising:
a location tracking system coupled to the vehicle and configured to determine a location of the vehicle.

8. The apparatus of claim 1, wherein the probe is coupled to a vehicle,
the apparatus further comprising:
a marking system coupled to the vehicle and configured to mark a location on a surface corresponding to test data produced using the probe.

9. The apparatus of claim 1, wherein the probe is coupled to a vehicle,
the apparatus further comprising:
a ground reference electrode coupled to the vehicle and functioning as a ground reference electrode, the ground reference electrode having a surface area at least two times larger than a surface area of the probe.

10. The apparatus of claim 1, further comprising:
a support, the interior rotating member being rotatably coupled about an axis to the support; and
a lift mechanism configured to move the support in a direction non-parallel to the axis.

11. The apparatus of claim 1, wherein the perimeter defined by the plurality of exterior rotating members surrounding the interior rotating member and aligned along a same plane as the interior rotating member.

12. The apparatus of claim 1, wherein each of the exterior rotating members includes a fluid retention portion made of a porous material configured to retain a fluid.

13. The apparatus of claim 1, wherein the interior rotating member includes a fluid retention portion electrically coupled via a top portion of the fluid retention portion and having a bottom portion defining at least a portion of a bottom surface of the probe.

14. The apparatus of claim 1, wherein the interior rotating member is physically separated by a gap from the plurality of exterior rotating members.

15. The apparatus of claim 1, further comprising:
a conductive member in contact with the interior rotating member or at least one of the plurality of exterior rotating members.

16. An apparatus, comprising:
a plurality of rotating members including:
a first rotating member configured to rotate about an axis, and
a second rotating member defining at least a portion of a guard ring around the first rotating member; and
a waveform generator electrically coupled via a first electrical path to the guard ring and electrically coupled via a second electrical path to the first rotating member.

17. The apparatus of claim 16, wherein the plurality of rotating members are coupled to a vehicle such that the plurality of rotating members are aligned along a plane,
the apparatus further comprising:
a movement mechanism coupled to the vehicle such that the vehicle moves the movement mechanism along a direction aligned along the plane.

18. The apparatus of claim 16, wherein each of the plurality of rotating members includes a fluid retention portion made of a porous material configured to retain a fluid.

19. The apparatus of claim 16, wherein each of the plurality of rotating members has a cylindrical shape or spherical shape.

20. The apparatus of claim 16, further comprising:
a conductive member in contact with the first rotating member or the second rotating member.

21. An apparatus, comprising: a probe configured to interrogate a surface and including an active probe and a guard ring disposed around the active probe, the active probe and the guard ring each being aligned along a plane; a waveform generator electrically coupled to the guard ring and the active probe; and a ground reference electrode configured to be disposed outside of the surface and made of a conductive material, the ground reference electrode having a surface area aligned along a plane and at least two times greater than a surface area of the probe.

22. The apparatus of claim 21, wherein the probe is a first probe and the guard ring is a first guard ring defining a first perimeter
the apparatus further comprising:
a second probe having a second guard ring defining a second perimeter physically separated from the first guard ring of the first probe,
the first probe and the second probe collectively having a surface area less than the surface area of the ground reference electrode.

23. The apparatus of claim 21, wherein at least one of the ground electrode or the probe includes a plurality of rotating members.

* * * * *